(12) United States Patent
Duan-Arnold et al.

(10) Patent No.: US 10,994,913 B2
(45) Date of Patent: *May 4, 2021

(54) SUPPORT AND PACKAGING FOR MEMBRANES

(71) Applicant: OSIRIS THERAPEUTICS, INC., Columbia, MD (US)

(72) Inventors: Yi Duan-Arnold, Ellicott City, MD (US); Alla Danilkovitch, Columbia, MD (US); Alexandra Gyurdieva, Elkridge, MD (US); Jin-Qiang Kuang, Glenelg, MD (US); Steven Michael Sinclair, Austin, TX (US)

(73) Assignee: Osiris Therapeutics, Inc., Columbia, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/279,413

(22) Filed: Feb. 19, 2019

(65) Prior Publication Data

US 2019/0276215 A1    Sep. 12, 2019

Related U.S. Application Data

(63) Continuation of application No. 14/657,535, filed on Mar. 13, 2015, now Pat. No. 10,279,974.

(Continued)

(51) Int. Cl.
*B65D 77/26* (2006.01)
*B65D 65/02* (2006.01)
(Continued)

(52) U.S. Cl.
CPC ............ *B65D 77/26* (2013.01); *A61F 2/0095* (2013.01); *A61F 15/001* (2013.01); *B65B 5/04* (2013.01);
(Continued)

(58) Field of Classification Search
CPC ........ B65D 77/26; B65D 77/24; B65D 65/00; B65D 65/02; B65D 5/04; B65D 5/06; B65D 55/22; A61F 2/0095
(Continued)

(56) References Cited

U.S. PATENT DOCUMENTS 4,231,357 A * 11/1980 Hessner ............. A61F 13/0206
602/47
4,649,909 A * 3/1987 Thompson ............. A61L 15/26
602/42

(Continued)

FOREIGN PATENT DOCUMENTS

CA       2942882        9/2016
CN    2015800215627    10/2016
(Continued)

OTHER PUBLICATIONS

U.S. Appl. No. 61/953,716, filed Mar. 14, 2014, Yi Duan-Arnold (Osiris Therapeutics, Inc.).

(Continued)

*Primary Examiner* — Steven A. Reynolds
*Assistant Examiner* — Javier A Pagan
(74) *Attorney, Agent, or Firm* — Norton Rose Fulbright US LLP

(57) ABSTRACT

A support assembly for supporting a biological product (e.g., membrane) in an operative position. The support assembly has a base and a cover. A membrane receiving portion of the base defines a plurality of perforations that extend between top and bottom surfaces of the product receiving portion. The cover is releasably coupled to the base in a product-covering position in which the cover overlies the product receiving portion of the base. In the operative position, the biological product engages the top surface of the product receiving portion and the bottom surface of the cover.

31 Claims, 11 Drawing Sheets

Related U.S. Application Data

(60) Provisional application No. 61/953,716, filed on Mar. 14, 2014.

(51) Int. Cl.
*B65D 85/00* (2006.01)
*B65B 5/04* (2006.01)
*B65B 55/22* (2006.01)
*A61F 2/00* (2006.01)
*A61F 15/00* (2006.01)
*A61F 2/10* (2006.01)
*A61B 90/00* (2016.01)

(52) U.S. Cl.
CPC .............. *B65B 55/22* (2013.01); *B65D 65/02* (2013.01); *B65D 85/70* (2013.01); *A61B 2090/0815* (2016.02); *A61B 2090/0816* (2016.02); *A61F 2/105* (2013.01)

(58) Field of Classification Search
USPC ........................................................ 206/570
See application file for complete search history.

(56) References Cited

U.S. PATENT DOCUMENTS

| | | | | |
|---|---|---|---|---|
| 5,100,671 | A | * | 3/1992 | Maeda .............. A61F 13/00063 424/443 |
| 5,465,735 | A | * | 11/1995 | Patel ..................... A61F 13/022 128/888 |
| D407,160 | S | * | 3/1999 | Dunshee ...................... D24/189 |
| 5,910,125 | A | * | 6/1999 | Cummings ......... A61F 13/0246 128/888 |
| D415,836 | S | * | 10/1999 | Dunshee ...................... D24/189 |
| D423,591 | S | * | 4/2000 | Conley .......................... D20/22 |
| D429,283 | S | * | 8/2000 | Conley .......................... D20/22 |
| D429,284 | S | * | 8/2000 | Conley .......................... D20/22 |
| 6,168,800 | B1 | * | 1/2001 | Dobos ..................... A61L 15/24 424/405 |
| D582,560 | S | * | 12/2008 | Sachi ........................... D24/189 |
| D776,823 | S | * | 1/2017 | Duan-Arnold .............. D24/189 |
| 10,279,974 | B2 | * | 5/2019 | Duan-Arnold ......... B65D 77/26 |
| 2007/0154515 | A1 | | 7/2007 | Johnson et al. |
| 2007/0207285 | A1 | * | 9/2007 | Lin ........................... B32B 7/14 428/40.1 |
| 2007/0224380 | A1 | * | 9/2007 | Ebisu ..................... B32B 33/00 428/40.1 |
| 2009/0093779 | A1 | * | 4/2009 | Riesinger .......... A61F 13/00029 604/290 |
| 2010/0063484 | A1 | | 3/2010 | Heagle |
| 2011/0021964 | A1 | * | 1/2011 | Larsen ................ A61L 26/0066 602/47 |
| 2011/0120477 | A1 | * | 5/2011 | Henderson .......... A61M 1/0088 128/850 |
| 2012/0125798 | A1 | | 5/2012 | Baecker et al. |
| 2013/0138069 | A1 | * | 5/2013 | Dewitt ................ A61F 13/0206 604/369 |
| 2014/0005793 | A1 | | 1/2014 | Koford et al. |

FOREIGN PATENT DOCUMENTS

| | | |
|---|---|---|
| EP | 2050474 A2 | 4/2009 |
| EP | 15762235.8 | 1/2017 |
| JP | 2016-557283 | 9/2016 |
| KR | 10-2016-7028653 | 10/2016 |
| WO | PCT/US2015/020502 | 3/2015 |

OTHER PUBLICATIONS

U.S. Appl. No. 14/657,535 (2015/0259119), filed Mar. 13, 2015 (Sep. 17, 2015), Yi Duan-Arnold (Osiris Therapeutics, Inc.).

International Search Report and Written Opinion dated Jun. 11, 2015 by the International Searching Authority for Application No. PCT/US2015/020502, which was filed on Mar. 13, 2015 and published as WO 2015/138935 on Sep. 17, 2015(Inventor—Duan-Arnold et al.; Applicant—Osiris Therapeutics, Inc.) (34 pages).

European Search Report dated Oct. 12, 2017 by the European Patent Office for Patent Application No. 15762235.8, which was filed on Mar. 13, 2015 and published as EP 3116459 on Jan. 18, 2017 (Inventor—Duan-Arnold et al.; Applicant—Osiris Therapeutics, Inc.) (7 pages).

Office Action dated Sep. 7, 2018 by the European Patent Office for Patent Application No. 15762235.8, which was filed on Mar. 13, 2015 and published as EP 3116459 on Jan. 18, 2017 (Inventor—Duan-Arnold et al.; Applicant—Osiris Therapeutics, Inc.) (3 pages).

International Preliminary Report on Patentability dated Sep. 14, 2016 by the International Searching Authority for Patent Application No. PCT/US2015/020502, which filed on Mar. 13, 2015 and published as WO 2015/138935 on Sep. 17, 2015 (Inventor—Duan-Arnold et al.; Applicant—Osiris Therapeutics, Inc.) (9 pages).

Restriction Requirement dated Oct. 26, 2016 by the U.S. Patent and Trademark Office for U.S. Appl. No. 14/657,535, filed Mar. 13, 2015 and published as US 2015/0259119 on Sep. 17, 2015 (Inventor—Duan-Arnold et al.; Applicant—Osiris Therapeutics, Inc.) (6 pages).

Restriction Requirement dated Sep. 6, 2017 by the U.S. Patent and Trademark Office for U.S. Appl. No. 14/657,535, filed Mar. 13, 2015 and published as US 2015/0259119 on Sep. 17, 2015 (Inventor—Duan-Arnold et al.; Applicant—Osiris Therapeutics, Inc.) (6 pages).

Non-Final Office Action dated Feb. 2, 2018 by the U.S. Patent and Trademark Office for U.S. Appl. No. 14/657,535, filed Mar. 13, 2015 and published as US 2015/0259119 on Sep. 17, 2015 (Inventor—Duan-Arnold et al.; Applicant—Osiris Therapeutics, Inc.) (12 pages).

Notice of Allowance dated Jul. 16, 2018 by the U.S. Patent and Trademark Office for U.S. Appl. No. 14/657,535, filed Mar. 13, 2015 and published as US 2015/0259119 on Sep. 17, 2015 (Inventor—Duan-Arnold et al.; Applicant—Osiris Therapeutics, Inc.) (7 pages).

Notice of Allowance dated Jan. 15, 2019 by the U.S. Patent and Trademark Office for U.S. Appl. No. 14/657,535, filed Mar. 13, 2015 and published as US 2015/0259119 on Sep. 17, 2015 (Inventor—Duan-Arnold et al.; Applicant—Osiris Therapeutics, Inc.) (9 pages).

Notice of Allowance dated Feb. 14, 2019 by the U.S. Patent and Trademark Office for U.S. Appl. No. 14/657,535, filed Mar. 13, 2015 and published as US 2015/0259119 on Sep. 17, 2015 (Inventor—Duan-Arnold et al.; Applicant—Osiris Therapeutics, Inc.) (2 pages).

* cited by examiner

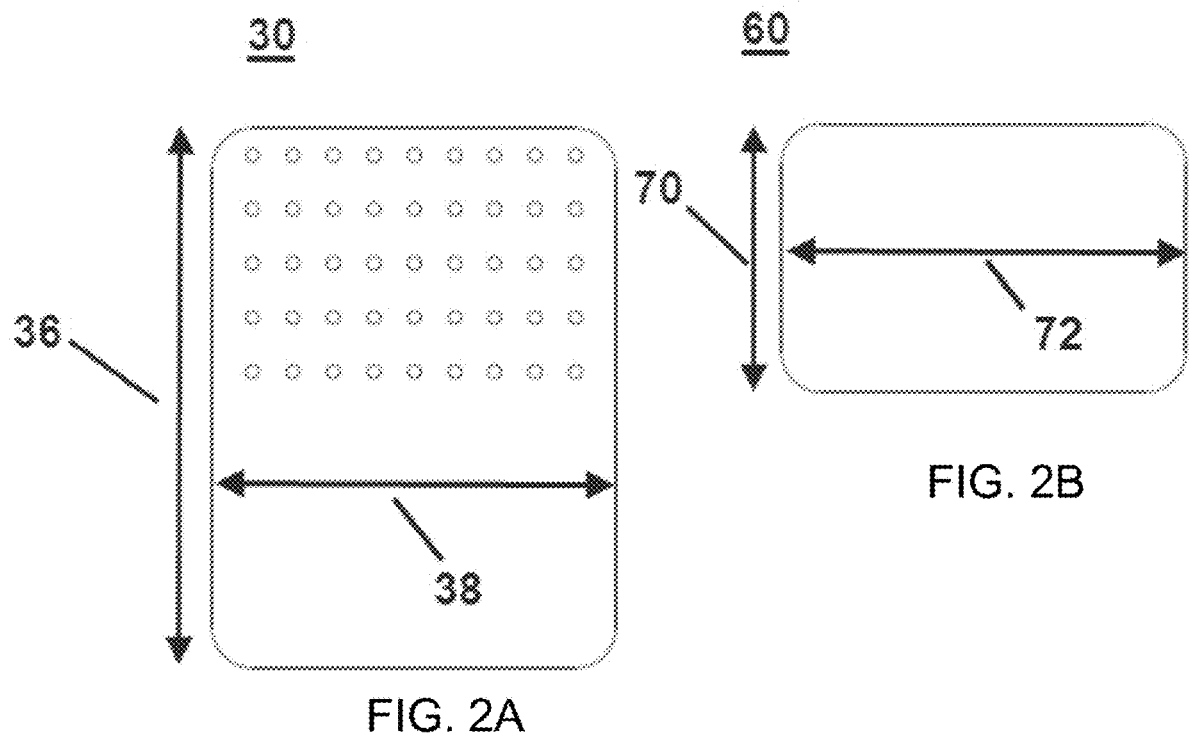
FIG. 2A
FIG. 2B
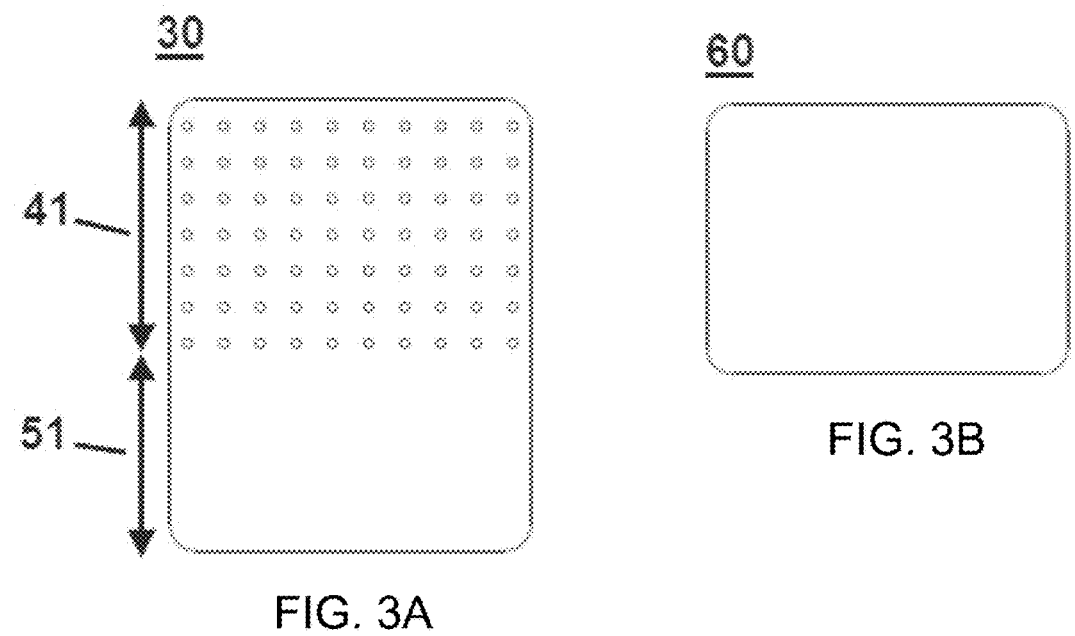
FIG. 3A
FIG. 3B

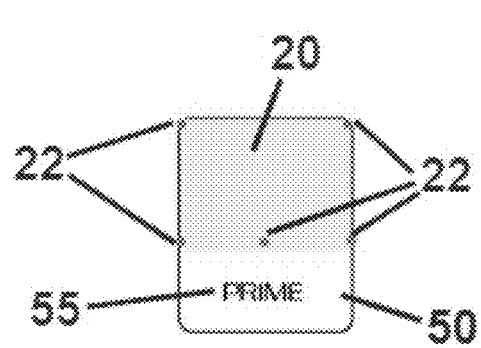
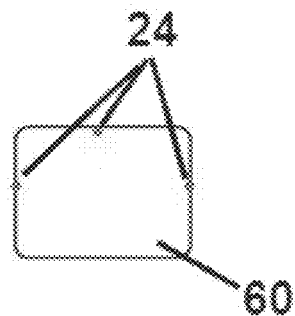
FIG. 6A  FIG. 6B
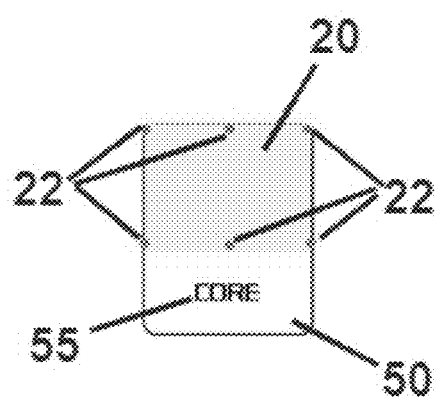
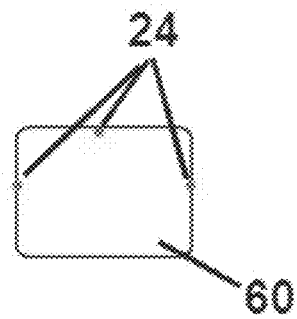
FIG. 7A  FIG. 7B
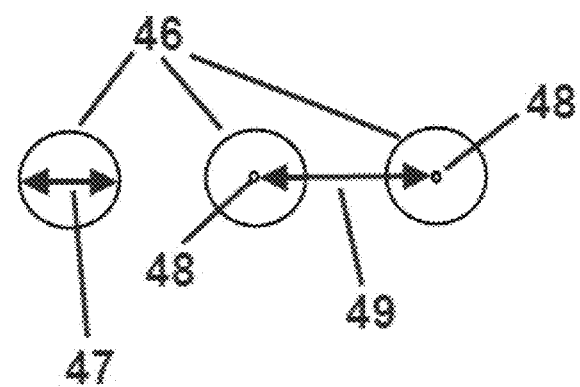
FIG. 8

| Schematic of perforation Prototype | Results |
|---|---|
| 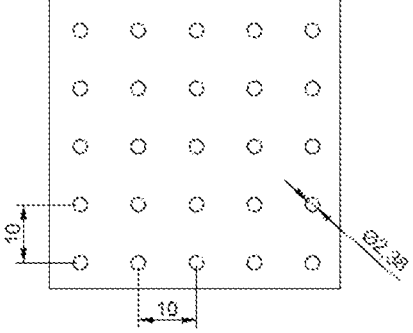 | Bond between amniotic membrane and plastic resulted in slightly compromised quadrant shape due to relatively weaker bond between the plastic and amniotic membrane |
| 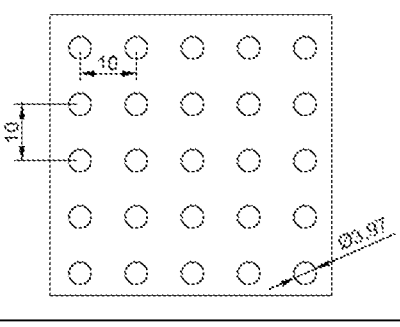 | Bond between amniotic membrane and plastic resulted in slightly compromised quadrant shape due to relatively weaker bond between the plastic and amniotic membrane |
| 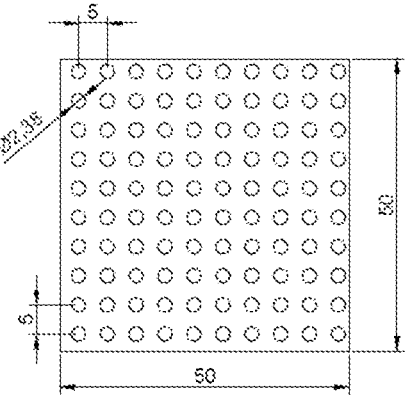 | Bond between amniotic membrane and plastic maintains the square shape, however >30% of amniotic membrane samples were detached from the plastic. |
| 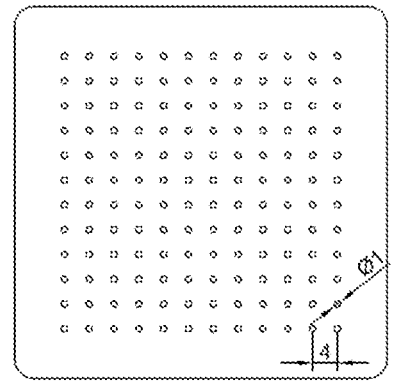 | Bond between amniotic membrane and plastic maintains the square shape.<br><25% of amniotic membrane samples detached from the plastic |

FIG. 10

| Schematic representation of perforation pattern | Number of perforations |
|---|---|
| 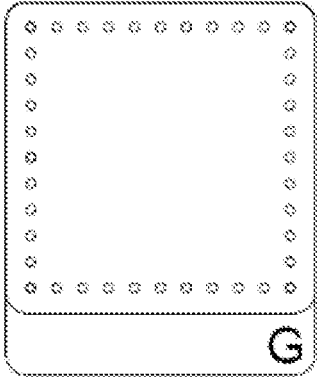 | 40 |
| 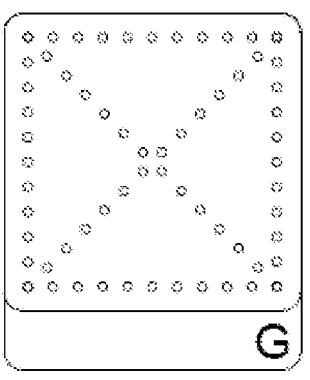 | 64 |
| 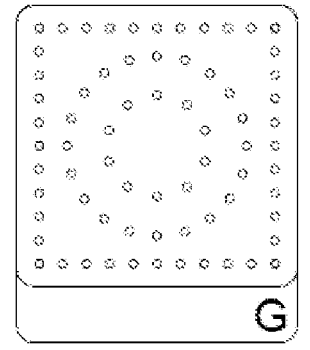 | 70 |
FIG. 11

| Number | Schematic Diagram | # cautery points |
|---|---|---|
| 1 |  | 8 |
| 2 |  | 7 |
| 3 |  | 6 |
| 4 |  | 8 |
| 5 |  | 8 |
| 6 |  | 9 |
| 7 | 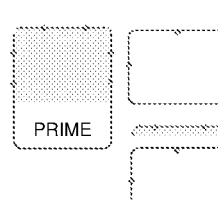 | 9 |
| 8 | 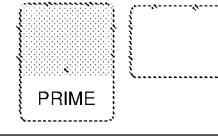 | 13 |
| 9 | 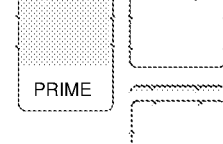 | 12 |
FIG. 12

| Design Number | Schematic Diagram | # of Cautery Points |
|---|---|---|
| 1 | 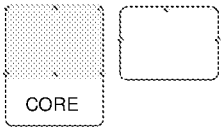 | 9 |
| 2 | 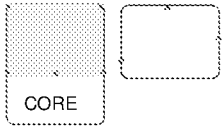 | 8 |
| 3 | 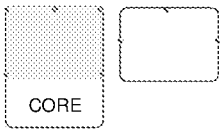 | 8 |
| 4 |  | 8 |
| 5 |  | 7 |
| 6 | 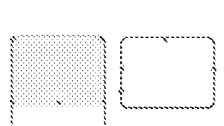 | 9 |
| 7 |  | 9 |
| 8 | 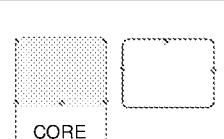 | 8 |
| 9 | 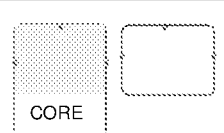 | 6 |
FIG. 13

SUPPORT AND PACKAGING FOR MEMBRANES

CROSS-REFERENCE TO RELATED APPLICATIONS

This application is a continuation of U.S. application Ser. No. 14/657,535, filed Mar. 13, 2015, now U.S. Pat. No. 10,279,974, which claims priority to and the benefit of the filing date of U.S. Provisional Patent Application No. 61/953,716, filed Mar. 14, 2014. Each of the above-identified applications is hereby incorporated herein by reference in its entirety.

BACKGROUND

Products are increasingly being used for treatment of wounds, burns, lacerations or surgical excisions. However, to use such products, there needs to be a method of manufacturing, packaging and applying the product that maintains the integrity of the product (including membranes) during these processes. Conventional packaging for applying a biological or membrane product does not lend itself to convenient application, and had multiple failings including its inability to provide real time sizing and directionality, among others. Conventional bandages and dressings, for example, fail to adequately protect large-scale, deep, oddly shaped and other types of wounds or tissue defects. Therefore, various alternatives have been explored in the art. Among these alternatives are split- and full-thickness grafts of cadaver or porcine skin, human allografts, cultured skin equivalents and autografts. Most of these membranes, including tissue or tissue equivalent products/synthetic products contain, in at least some aspects, a morphology similar to actual human skin, which has an epithelial layer on the top and connective tissue with fibroblasts or other types of cells on the bottom facing the wound and/or damaged tissue. Such products can be considered to have directionality. Further, when such membranes are used to treat a variety of wounds (or tissue defects), the preferred orientation of the wound, tissue, graft or applied biological product is such that the connective tissue layer rests on the wound bed while the epithelial layer is away from the wound bed.

Challenges exist with conventional packaging systems for the storage, transport and the delivery or application of membranes to various human or animal structures needing treatment such as wounds or tissue defects. For example, the tensile strength of the grafts, tissues, or membranes is such that they often cannot support their own weight and tear if suspended by an edge. For this reason, these types of graft, tissue or membrane products are often mounted on a carrier paper and then packaged into a sealable container (such as a bag), which contains a substantial amount of liquid (e.g., a biomedium such as a biosolution or bioprotectant). Typically, the attachment of the graft to the carrier paper, however, is relatively weak. Thus, during manufacture, transportation to its end use site, and finally during handling prior to application to a wound (or tissue defect), the tissue or membrane may separate from the carrier paper voluntarily or inadvertently, due to shear forces of liquid moving around in the overall packaging. As a result, the tissue, graft or membrane to be applied may curl, attach to itself, attach to other aspects of the packaging, tear, or in some other fashion become unusable for final application to the human or animal. This results in significant waste, time loss, patient and/or care provider dissatisfaction and cost, and ineffective therapeutic treatment of the wound or tissue defect, among other negative attributes. In addition, if a graft or membrane product being supplied is cryopreserved, complete thawing of all ice crystals (e.g., of the biomedium or cryoprotectant contained in the container along with the tissue, graft, or membrane to be finally applied) is necessary prior to the product's final application to a human or animal. This thawing procedure can last for several minutes (e.g., up to 30 minutes or more) depending upon the volume of liquid and other material to be thawed within the packaging. This thawing wait time and additional procedure make such conventional tissue, graft or membrane products and product packaging inconvenient for health care providers who may be treating several wounds during any given period of time.

Finally, concerns also exist with current conventional application and delivery of tissue, graft or membrane-based products/systems/packages. If the membrane, tissue or graft needs to be separated from the packaging (e.g., a carrier paper or carrier bottom paper) and at the same time kept in a proper orientation (e.g., epithelial on top and connective tissue on the bottom) for delivery to the patient site such as a wound (or tissue defect), then the packaging must so indicate in a clear manner and be capable of maintaining that orientation during manufacture, transit and final application. This becomes even more difficult to achieve when the size of the supplied graft, tissue or membrane is small. Once the graft, tissue or membrane folds over upon itself (or becomes disorientated in some other fashion), it is very difficult to restore the biological material to its original planar configuration, for example, and essentially impossible to make the appropriate final application to the wound.

Therefore, there is a need within the art for a new package, packaging system, composition, device, article of manufacture and method of delivery utilizing such materials that overcomes these deficiencies within the conventional art.

SUMMARY

Described herein, in one aspect, is a support assembly for supporting a biological product (e.g., a membrane) in an operative position. The support assembly can have a base and a cover. The base can have a longitudinal axis and comprise a product receiving portion. The product receiving portion can have a top surface and an opposed bottom surface that are spaced apart relative to a vertical axis that is perpendicular to the longitudinal axis of the base. The product receiving portion can have at least one traction-creating feature, which can be selected from the group consisting of (i) a rough top surface; and (ii) a plurality of perforations that extend between the top and bottom surfaces of the product receiving portion. The cover can have a longitudinal axis, a top surface, and an opposed bottom surface. The cover can be configured for releasable coupling (optionally, attachment) to the base in a product-covering position. In the product-covering position, the cover overlies the product receiving portion of the base. The base and the cover can be configured to cooperate to support the biological product in the operative position. In the operative position, the biological product is positioned in engagement with at least a portion of the top surface of the product receiving portion of the base and at least a portion of the bottom surface of the cover.

In another aspect, described herein is a membrane product package comprising a membrane and a support assembly as disclosed herein. The membrane product package includes a membrane that is positioned in an operative position between the product receiving portion of the base and the cover. The membrane can be positioned in engagement with at least a portion of the top surface of the product receiving portion of the base and at least a portion of the bottom surface of the cover.

Also described is a method of producing a membrane product package as disclosed herein. The method can comprise positioning a membrane in an operative position between the product receiving portion of the base and the cover of a support assembly as disclosed herein. The membrane can be positioned in engagement with at least a portion of the top surface of the product receiving portion of the base and at least a portion of the bottom surface of the cover.

Additionally, described herein is a method of applying a membrane using a membrane product package as disclosed herein. The method can comprise removing the cover from the membrane product package to expose a top surface of the membrane. Following removal of the cover, the membrane can remain in the operative position, which generally corresponds to the orientation in which the membrane is to be applied. The method can further comprise sliding the membrane relative to the top surface of the product receiving portion of the base to disengage the membrane from the top surface of the product receiving portion of the base and permit selective application of the membrane as further disclosed herein.

Further described is a kit for repairing a tissue defect. The kit can comprise a membrane product package as disclosed herein and instructions for applying the membrane to repair the tissue defect.

More generally, in some aspects and embodiments, the present technology provides a device (e.g., a support assembly), composition (e.g., a membrane product package), article of manufacture or system comprising: a base comprising at least one product (e.g., membrane) receiving portion; a cover; and at least one location in which the base and the cover are in communication (e.g., coupled to one another through a membrane or attached to one another as further disclosed herein). In some embodiments, the device, composition, article of manufacture or system further comprises a membrane, tissue, graft or other biological material (s) temporarily connected, attached, adhered, or operatively associated with the cover, the base or both. The base and the cover can be positioned in communication via at least one temporary or removable attachment between the base and the membrane, the membrane and the cover, and/or the base and the cover.

In some aspects or embodiments, the product (e.g., membrane) receiving portion of the present technology comprises a structured surface that is configured to promote adhesion of a membrane or other biological product to the product receiving portion as further disclosed herein. Such structured surfaces are referred to herein as "traction-creating features." In other aspects or embodiments of the present technology, the traction-creating features can include one or more of a rough surface; a plurality of perforations; a surface comprising a plurality of channels; a surface comprising a plurality of grooves; a surface comprising a plurality of indentations; or a surface comprising a plurality of porations. In exemplary aspects, the rough surface can be one or more of an abraded surface, a scratched surface, an uneven surface, a gritty-type surface (yet, preferably free or substantially free of loose particulate), or a bumpy surface, among others. In some aspects, the traction-creating feature comprises at least one perforation, at least one channel, at least one groove or at least one indentation, wherein, in some instances, the at least one perforation, at least one channel, at least one groove and/or at least one indentation has a complex pattern. In some aspects or embodiments, the base further comprises a handling portion, which can optionally be adjacent to the membrane receiving portion. In further aspects or embodiments, the handling portion does not overlap with the cover. In still further aspects or embodiments, the handling portion comprises at least one tab. In some aspects or embodiments, the tab spans the entire width of the base. In other aspects or embodiments, the cover spans the entire product (e.g., membrane) receiving portion of the base. However, segments, portions or parts of the width of the base or membrane receiving portion are also envisaged.

In additional aspects or embodiments, the at least one location in which the base and cover are in communication (preferably temporarily) with each other comprises, for example, at least one cauterization point, at least one point made by an ultrasonic welder, or at least one point comprising a biocompatible adhesive. In other aspects or embodiments, the at least one location in which the base and cover are in communication (preferably temporary communication) with one another comprises a plurality of points. In still further aspects and embodiments of the present technology, the base and the cover are formed from a single piece of biocompatible plastic or other suitable biopolymer suitable for use with membranes, tissues, grafts, or other biological materials. In additional aspects or embodiments of the present technology, the base and the cover are separate pieces of biocompatible plastic or biopolymer or other biocompatible material. In other aspects or embodiments, the base and the cover are made of the same type of biocompatible plastic or other biopolymer, biocopolymer or other biocompatible material.

Some aspects of the present technology provide a composition comprising: a base comprising at least one membrane receiving portion; at least one membrane; at least one cover; and at least one location in which the base and the cover are in communication, wherein the membrane is positioned between the base and the cover. In other aspects or embodiments, the base further comprises at least one handling portion. In still further aspects or embodiments, the handling portion can be adjacent to the membrane receiving portion.

Moreover, additional aspects or embodiments of the present technology provide a cryopreserved membrane composition comprising: a) any of the compositions, devices, articles of manufacture, devices or systems of the present technology disclosed herein; and b) at least one cryopreservation medium or other compatible biological medium.

In other instances of the present technology a kit is provided comprising: any of the devices, articles of manufacture, compositions, or systems of the present technology described herein; and instructions or guides for sizing, orienting, and/or applying, connecting or adhering at least one membrane between the base and the cover of the device, wherein the base and the cover have at least one location which is adapted to be in communication with each other. Alternatively, these aspects and embodiments of the present technology can also include at least one, preferably more than one, point of connection between the cover and the membrane, the base and the membrane, and/or the cover and the base. Additionally, the kit aspects and embodiments of the present technology can further comprise an adhesive. The adhesive may be an adhesive that is biologically compatible, or other suitable biocompatible materials to connect the cover and the base, to connect the base to the membrane, or to connect the membrane-covered base to the cover. The adhesive may be biocompatible, able to withstand physical or chemical alterations by solutions and solvents (e.g., a cryopreservation solution), and/or to withstand a wide range of temperatures (for example, from about 60° C.±5° C. to about −196° C.±5° C., as described herein.

In some aspects or embodiments of the present technology pertaining to a kit, instructions can further comprise at least one method of temporarily adhering, connecting, or applying the base to a first side of the membrane, wherein the method comprises applying at least one biocompatible adhesive to at least one location between the base and a first side of the membrane to form a temporary bond between the membrane and the base. In some instances, the instructions further comprise methods of applying the at least one adhesive to at least one location on a first side of a cover and the second side of the membrane to temporarily bond the cover to the second side of the membrane, forming a cover-membrane-base configuration.

In other aspects, the instructions included with the kits of the present technology provide a method of temporarily and sufficiently coupling (e.g., connecting, attaching, applying, adhering, or indirectly securing through the membrane) the cover to the base wherein the membrane is located between the cover and base (e.g., similar to a sandwich-like configuration), wherein the method further comprises applying at least one adhesive (or other biocompatible material) to at least one point between the cover and the membrane-covered base and/or between the cover and the membrane.

It should be appreciated by those skilled in the art that other attachment mechanisms and methods can be utilized to attach the cover to the base as well as the cover to the membrane and to attach the base to the membrane as well as the cover and base to the membrane. For example, in some aspects and embodiments of the present technology, the kit includes instructions for cauterizing at least one point of the cover to the base, wherein the membrane is located between the cover and base. In some instances, the instructions provide a method of cauterizing the membrane to the base at least at one point, alternatively at least at two points, alternatively at least at three points, alternatively at least at four points, alternatively at least at five points, alternatively at least at six points. In other instances, the instructions further provide instructions on cauterizing the cover to the membrane-base at least at one point, alternatively at two points, alternatively at least at three points. The instructions provide a method of cauterizing the cover, membrane and base such that the membrane is disposed between the cover and base. In alternative aspects or embodiments of the present technology, the instructions can further comprise at least one method of maintaining the directionality of the membrane, the method comprising the step of adhering a first side of the membrane to the base in a specific orientation and/or direction desired (e.g., in the operative position).

In still further aspects or embodiments of the present invention, the kit can also further comprise at least one set of instructions for cryopreserving the device, composition, article of manufacture or system of the present technology comprising at least one membrane to be cryopreserved. With respect to these particular aspects and embodiments, the cryopreservation step comprises, for example, cryofreezing the device, composition, article of manufacture, or system of the present technology containing the membrane at about −18 to −20° C.±5° C. to about −196° C.±5° C., in some aspects from about −80° C. to about −196° C.±5° C. For acellular membranes, freezing may take place from about −18-−20° C.±5° C. to about −196° C.±5° C. For membranes containing viable cells, freezing may take place from about −45° C.±5° C. to about −196° C.±5° C. In aspects or embodiments of the present technology, the kit can further comprise instructions for thawing the cryopreserved membrane while a component of the device, composition, article of manufacture, or system described herein.

In some aspects, the kit further comprises instructions for applying the membrane to a human or animal in need thereof.

In some instances, the present technology provides a kit for repairing a tissue defect comprising: a cryopreserved composition, device, article of manufacture, or system described herein; and instructions for applying the cryopreserved membrane or biological material to the tissue defect. In some aspects, the kit further comprises instructions for thawing the cryopreserved composition. In some aspects, the kit comprises further instructions on maintaining the directionality of the membrane while being applied to the tissue defect. In some aspects, the kit further comprises instructions for removal of the cover. In some aspects, the kit further comprises instructions for maintaining the directionality of the membrane. In some aspects, the kit further comprises instructions for removing the membrane from the base.

In further instances, the present technology provides a method of maintaining the directionality of a membrane during storage, cryopreservation, or during application to a subject comprising: preparing a membrane, wherein the membrane is orientated having a first and a second side (e.g., a top surface and a bottom surface), wherein the first and second side comprise different compositions, structures or properties; b) adhering the membrane to the device, system or article of manufacture described herein comprising a base and a cover, wherein the membrane is disposed between the base and the cover; and wherein the first side of the membrane is facing the base and the second side of the membrane is facing the cover; and wherein device further comprises a label to indicate orientation.

In still other aspects, described herein is a method of applying a membrane to a human or animal in need thereof, comprising: obtaining a composition, system or article of manufacture as described herein which has been cryopreserved and frozen; thawing the composition, system or article of manufacture; optionally rinsing the membrane in a sterile physiological solution; removing the cover from the membrane and base; and applying the membrane from the base onto the human or animal to retain directionality of the membrane.

In yet further instances, the present technology provides a method of maintaining integrity of a membrane during cryopreservation, comprising: providing a device as described herein; adhering a membrane to at least an area of the membrane receiving portion of the base; adhering the cover to the base (optionally, through the membrane, which can be directly adhered to the base), wherein the membrane is between the cover and the base; and placing the device comprising the membrane into a container; and contacting the container with sterile cryopreservation solution, wherein the device comprising the membrane is submerged in the cryopreservation solution; and cryopreserving the container at a temperature of about −80° C. to about −196° C., wherein the integrity of the membrane is maintained once the membrane is thawed to room temperature.

In some aspects, described is a method of treating a wound comprising applying a membrane of any one of the compositions, systems or articles of manufacture described herein to a human or animal in need thereof.

Some aspects provide a system comprising: a base comprising a membrane receiving portion; and a cover; and at least one location in which the base and the cover are in communication. In some aspects, the system further comprises a membrane, wherein the membrane is disposed between the cover and the base. In these aspects, the base and the cover can be in communication at least one attachment point (at least one temporary or removable attachment between the base and the cover, the base and the membrane, and/or the cover and the membrane).

In some aspects, an article of manufacture comprising: a base comprising a membrane receiving portion; and a cover; and at least one location in which the base and the cover are in communication (at least one temporary or removable attachment between the base and the cover, the base and the membrane, and/or the cover and the membrane).

The present technology will be described in more detail below with regard to the devices, compositions, articles of manufacture, devices, systems and methods of utilizing each for the protection of tissues, membranes or graft materials, for example, during manufacture, processing, cryopreservation, storage, and transport.

DESCRIPTION OF THE DRAWINGS

FIG. 1A is a top view depicting the base of the support assembly, and FIG. 1B is a top view depicting the cover of the support assembly.

FIGS. 2A and 2B depict the base and the cover of another exemplary support assembly as disclosed herein. FIG. 2A is a top view depicting the base of the support assembly, and FIG. 2B is a top view depicting the cover of the support assembly.

FIGS. 3A and 3B depict the base and the cover of another exemplary support assembly as disclosed herein. FIG. 3A is a top view depicting the base of the support assembly, and FIG. 3B is a top view depicting the cover of the support assembly.

FIG. 4A is a top view depicting the base of the support assembly, and FIG. 4B is a top view depicting the cover of the support assembly.

FIG. 5A is an exploded view of the membrane product package, showing the relative orientation of the base, the membrane, and the cover. FIG. 5B is a top view of the base, showing the membrane positioned in engagement with the product receiving portion of the base. FIG. 5C is a top view of the membrane product package following positioning of the cover over the membrane, thereby supporting the membrane between the cover and the product receiving portion of the base. As shown, the membrane can be attached to the base and the cover at a plurality of attachment points as disclosed herein.

FIGS. 6A-6B depict an exemplary configuration of attachment points on an exemplary support assembly as disclosed herein. FIG. 6A is a top view depicting the attachment points on the base of the support assembly, and FIG. 6B is a top view depicting the attachment points on the cover of the support assembly.

FIGS. 7A-7B depict an exemplary configuration of attachment points on another exemplary support assembly as disclosed herein. FIG. 7A is a top view depicting the attachment points on the base of the support assembly, and FIG. 7B is a top view depicting the attachment points on the cover of the support assembly.

FIG. 8 is an isolated top view of a plurality of perforations of the product receiving portion of a base, as disclosed herein.

FIG. 10 is a schematic representation of the perforation size and center-to-center spacing between perforations on amniotic membrane handling properties.

FIG. 11 is a schematic representation of the perforation pattern on the ability to maintain more than 75% membrane on the base after removal of the cover.

FIG. 12 is a schematic representation of the cautery patterns for amniotic membranes.

FIG. 13 is a schematic representation of the cautery patterns for chorionic membranes.

DETAILED DESCRIPTION

Figures 1A, 1B:
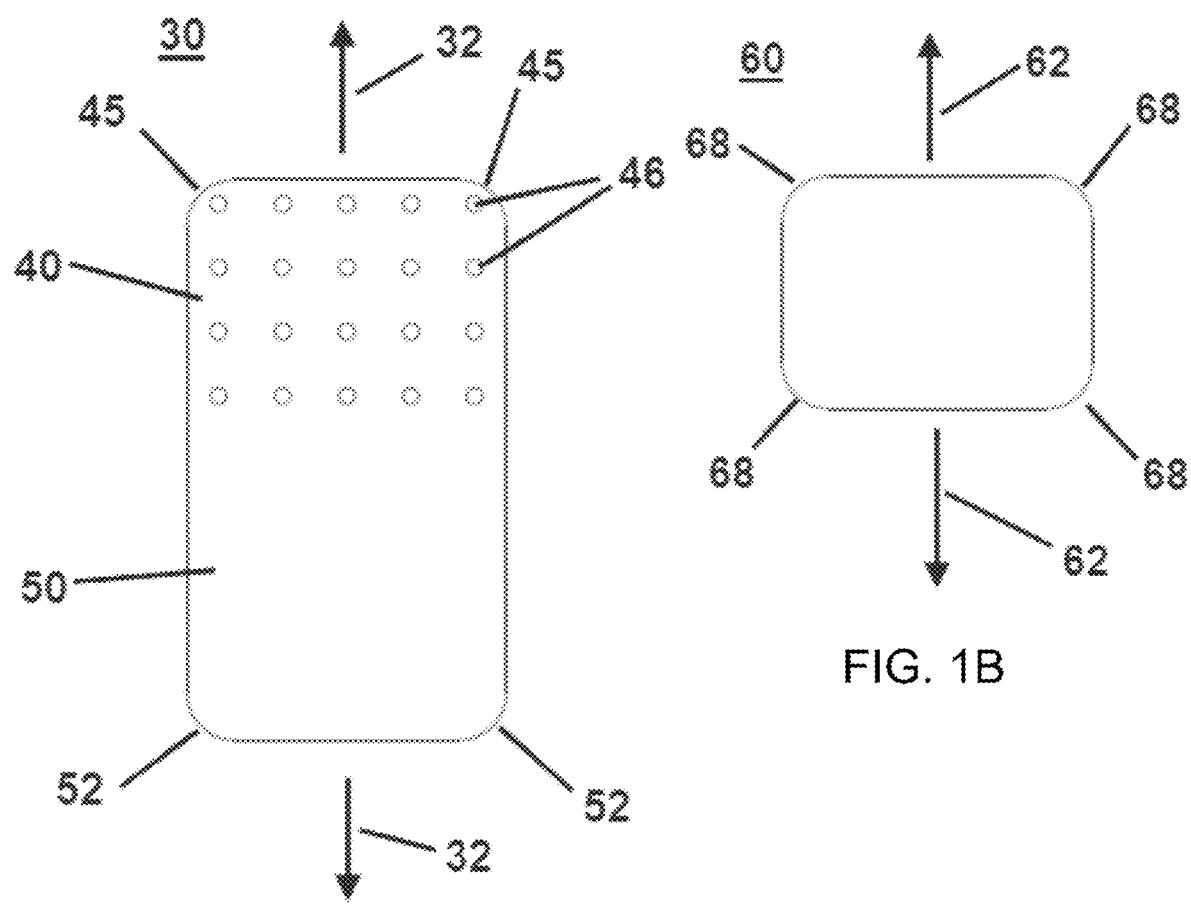
FIGS. 1A and 1B depict the base and the cover of an exemplary support assembly as disclosed herein.
Figure 4A:
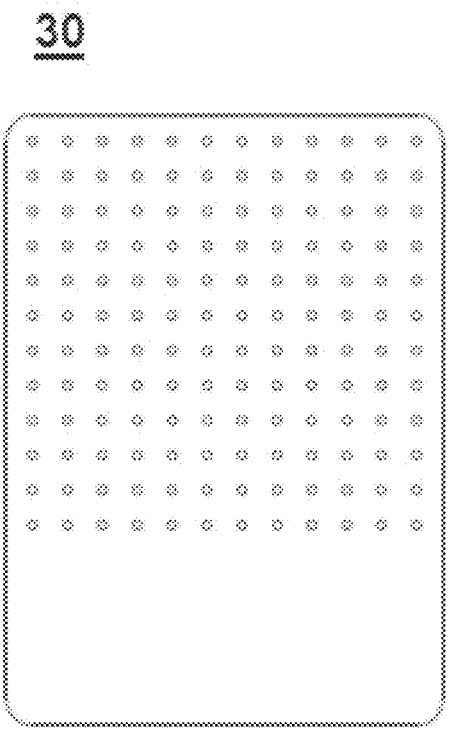
FIGS. 4A and 4B depict the base and the cover of another exemplary support assembly as disclosed herein.
Figure 4B:
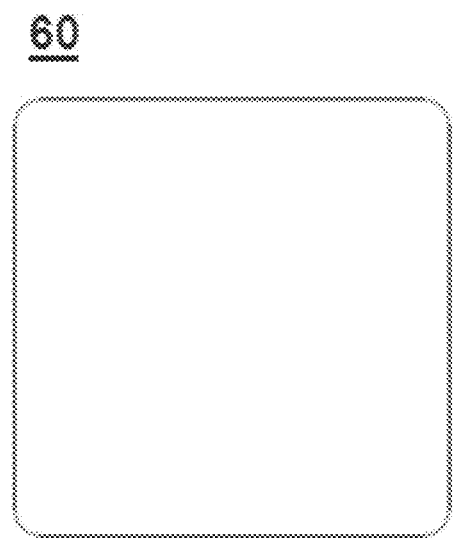

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout. It is to be understood that this invention is not limited to the particular methodology and protocols described, as such may vary. It is also to be understood that the terminology used herein is for the purpose of describing particular embodiments only, and is not intended to limit the scope of the present invention.

Many modifications and other embodiments of the invention set forth herein will come to mind to one skilled in the art to which the invention pertains having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

As used herein the singular forms "a", "an", and "the" include plural referents unless the context clearly dictates otherwise. Thus, for example, reference to "a cover" can include a plurality of such covers, and so forth. All technical and scientific terms used herein have the same meaning as commonly understood to one of ordinary skill in the art to which this invention belongs unless clearly indicated otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The word "or" as used herein means any one member of a particular list and also includes any combination of members of that list.

As used herein, the terms "product receiving portion" and "membrane receiving portion" are used interchangeably, with it being understood that both terms refer to a region of the base of a support assembly or membrane product package as disclosed herein that is configured to engage a surface of a biological product (e.g., membrane) as disclosed herein and to cooperate with the cover of the support assembly to support the biological product in an operative position.

As used herein, the term "support assembly" generally refers to the combination of a base and a cover as disclosed herein.

As used herein, the term "membrane product package" generally refers to the combination of a base, a cover, and a membrane positioned between the base and the cover, as further disclosed herein.

As used herein, the term "traction-creating feature" refers to a structural feature of the product receiving portion of a base as disclosed herein that exhibits a high affinity for a biological product (e.g., membrane) and/or that promotes adhesion, coupling, or other operative contact between a biological product (e.g., membrane) and the product receiving portion as further disclosed herein, which can produce surface traction between the top surface of the product receiving portion of the base and the product (e.g., membrane) to prevent undesired movement of the product relative to the base. Exemplary traction-creating features include a rough surface; a plurality of perforations; a surface comprising a plurality of channels; a surface comprising a plurality of grooves; a surface comprising a plurality of indentations; or a surface comprising a plurality of porations. Optionally, in use, it is contemplated that the perforations, channels, grooves, indentations, porations, and other void spaces can effectively create a suction force that adheres the biological product (e.g., membrane) to the product receiving portion, whereas the rough surfaces disclosed herein can mechanically (e.g., frictionally) engage the bottom surface of the biological product (e.g., membrane) to resist movement of the product relative to the base. Examples of such a "rough surface" include, for example and without limitation, an abraded surface, a scratched surface, an uneven surface, a gritty-type surface (yet, preferably free or substantially free of loose particulate), or a bumpy surface, among others. Optionally, it is contemplated that the product receiving portion can comprise a combination of different rough surfaces that cooperate to define the product receiving portion.

Overview

The present technology provides compositions, articles of manufacture, devices, systems and methods of utilizing each for the protection of tissues, membranes, or graft materials, for example, during manufacture, processing, cryopreservation, storage and transport to the health care provider/health care provider site. Further, the present technology provides compositions, articles of manufacture, devices, systems and methods of utilizing each for the delivery or application of tissues, membranes, other biological materials and grafts to a human or animal in need thereof. In particular, the present technology provides compositions, articles of manufacture, devices, systems and methods of utilizing each for the treatment of wounds, tissue defects or membrane defects or injuries in a human or animal. Further, the present technology provides compositions, articles of manufacture, devices, systems and methods of utilizing each for the preparation, storage, transportation and delivery of tissue, membrane, grafts or other biological products for others uses, including but not limited to diagnostics, experimental testing and the like.

The present technology in at least some aspects and embodiments comprises a device, composition, article of manufacture or system (namely in the form of packaging) comprising at least a base and a cover suitable for use with a biological membrane, tissue or graft (or other biological material) that can support, stabilize and protect such biological materials during manufacture, storage, transportation and delivery/application (preferably by a health care provider) to an end user (i.e., a human or animal patient) or wound. Generally, the present technology also comprises at least one location wherein the base and cover are in communication with one another. Such communication between the base and the cover can optionally be separate from the communication that the base and the cover have with a tissue, membrane, graft or other biological material as disclosed herein. Further, it should be appreciated by those skilled in the art that the present technology also provides devices, compositions, articles of manufacture and systems that can be used multi-functionally as a carrier for a membrane, tissue, other biological material or graft during the resultant packaging's or packaging system's manufacture and storage, including for example, during cryopreservation and thawing of the associated membrane, tissue, graft, or other biological materials. Moreover, the present technology provides at least one device, article of manufacture, composition and/or system that allow for a desired orientation (i.e., directionality, spatial arrangement, and/or positioning) of the membrane, tissue, biological material or graft material that is temporarily applied, supported, associated, or affixed thereto in some manner or fashion.

Disclosed herein with reference to FIGS. 1A-8 is a support assembly for supporting a biological product (e.g., membrane) 20 in an operative position. In exemplary aspects, the support assembly can comprise a base 30 and a cover 60.

In one aspect, and with reference to FIGS. 1A, 2A, 3A, 4A, and 5A-5C, the base 30 can have a longitudinal axis 32 and comprise a product (e.g., membrane) receiving portion 40. In this aspect, the product receiving portion 40 can have a top surface 42 and an opposed bottom surface 44 that are spaced apart relative to a vertical axis 34 that is perpendicular to the longitudinal axis 32 of the base 30. In exemplary aspects, the product receiving portion 40 of the base 30 can comprise at least one traction-creating feature that is configured to promote surface traction between a product (e.g., membrane) and the base. Optionally, in one exemplary aspect, the traction-creating feature of the product receiving portion 40 can be selected from the group consisting of (i) a rough top surface 80 as further disclosed herein (see FIG. 9); and (ii) a plurality of perforations 46 that extend between the top and bottom surfaces 42, 44 of the product receiving portion. Thus, in some optional aspects, the product receiving portion 40 can comprise a rough top surface 80, while in other optional aspects, the product receiving portion 40 can define a plurality of perforations 46.

Figure 5A:
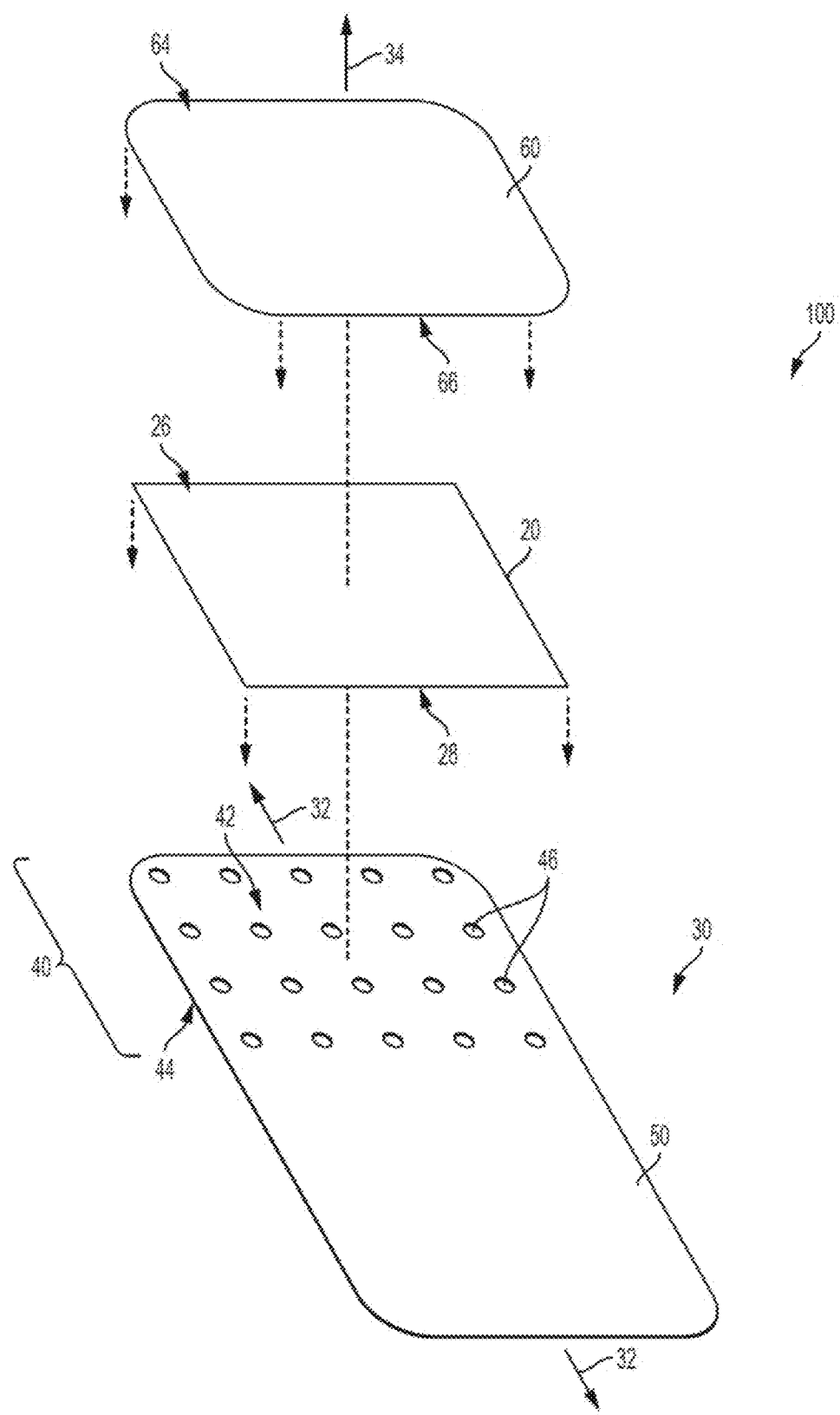
FIGS. 5A-5C schematically depict the assembly of a membrane product package as disclosed herein.
Figure 5B:
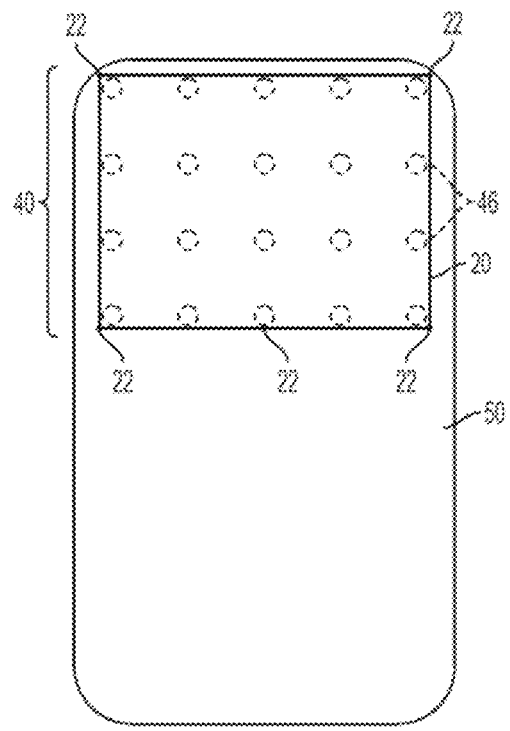
Figure 5C:
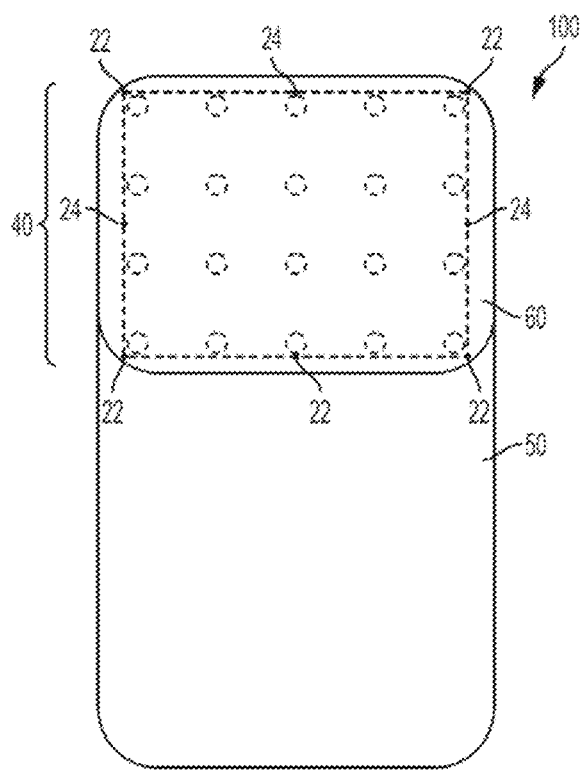

In another aspect, and with reference to FIGS. 1B, 2B, 3B, 4B, and 5A, the cover 60 can have a longitudinal axis 62, a top surface 64, and an opposed bottom surface 66. In this aspect, and as further disclosed herein, the cover 60 can be configured for releasable coupling (optionally, releasable attachment) to the base 30 in a product-covering position. As shown in FIG. 5C, in the product-covering position, the cover 60 can overlie the product receiving portion 40 of the base 30 and any product (e.g., membrane) 20 positioned over the product receiving portion. In exemplary aspects, the base 30 and the cover 60 are configured to cooperate to support the biological product 20 in the operative position. With reference to FIGS. 5A-5C, in the operative position, the biological product 20 is positioned in engagement with at least a portion of the top surface 42 of the product receiving portion 40 of the base 30 and at least a portion of the bottom surface 66 of the cover 60. As further disclosed herein, it is contemplated that the operative position can correspond to a desired orientation of the product 20, such as, for example and without limitation, an advantageous orientation for application of the product 20 to a human or animal patient.

In a further aspect, the base 30 can further comprise a handling portion 50 that is positioned adjacent to the product receiving portion 40 relative to the longitudinal axis 32 of the base. Optionally, in exemplary aspects, in the product-covering position, the cover 60 does not overlap with the handling portion 50 of the base 30. In further optional aspects, the handling portion 50 can comprise a tab. In an exemplary aspect, the handling portion 50 of the base 30 can have a longitudinal length 51 and a width, wherein the product receiving portion 40 of the base has a longitudinal length 41 and a width, and wherein the width of the product receiving portion is equal to the width of the handling portion (see FIG. 2A, showing the base 30 having a constant width 38). Optionally, in some aspects, the longitudinal length 41 of the product receiving portion 40 can be greater than the longitudinal length 51 of the handling portion 50. Optionally, in other aspects, the longitudinal length 41 of the product receiving portion 40 can be less than the longitudinal length 51 of the handling portion 50. In further optional aspects, the longitudinal length 41 of the product receiving portion 40 can be substantially equal to the longitudinal length 51 of the handling portion 50. As one will appreciate, in combination, the longitudinal length 41 of the product receiving portion 40 and the longitudinal length 51 of the handling portion 50 can define a longitudinal length 36 of the base 30. However, in some optional aspects, and as further disclosed herein, it is contemplated that the product receiving portion 40 can extend along substantially the entire longitudinal length 36 of the base 30, in which case the longitudinal length 41 of the product receiving portion will be substantially equal to the longitudinal length of the base.

Optionally, in an additional aspect, in the product-covering position, the longitudinal axis 62 of the cover 60 can be positioned in substantial alignment with the longitudinal axis 32 of the base 30. In another aspect, the cover 60 can have a longitudinal length 70 and a width 72. Optionally, in this aspect, the longitudinal length 70 of the cover 60 can be substantially equal to the longitudinal length 41 of the product receiving portion 40. Optionally, it is further contemplated that the width 72 of the cover can be substantially equal to the width 38 of the product receiving portion.

In a further aspect, and with reference to FIGS. 1A-1B, the cover 60 can have a plurality of corners 68. Optionally, in this aspect, at least one of the corners 68 of the cover is rounded. In exemplary aspects, it is contemplated that the cover 60 can have four rounded corners 68. However, it is contemplated that the corners 68 can have other sharp or non-sharp profiles, such, as for example and without limitation, a beveled profile. In further exemplary aspects, it is contemplated that the product receiving portion 40 of the base 30 can have two rounded corners 45. In these aspects, it is contemplated that, in the product-covering position, two rounded corners 68 of the cover 60 can overlie the two rounded corners 45 of the product receiving portion 40 of the base 30. It is further contemplated that the handling portion 50 of the base 30 can have two corners (optionally, rounded corners) 52 that are positioned in opposition to the corners 45 defined by the product receiving portion 40.

In exemplary aspects, the plurality of perforations 46 of the product receiving portion 40 of the base 30 can be substantially evenly distributed throughout the product receiving portion.

In further exemplary aspects, the plurality of perforations 46 of the product receiving portion 40 of the base 30 can be randomly distributed throughout the product receiving portion.

In an additional aspect, and with reference to FIG. 8, each perforation 46 of the plurality of perforations can have a respective diameter 47. Optionally, in exemplary aspects, the diameter 47 of each perforation 46 can range from about 0.1 mm to about 5 mm. Optionally, it is contemplated that the perforations 46 can have substantially equal diameters. However, it is further contemplated that at least one perforation 46 of the plurality of perforations can have a diameter 47 that is substantially different than the diameter of at least one other perforation.

In another aspect, and with reference to FIG. 8, each perforation 46 of the plurality of perforations can have a respective center point 48. Optionally, in this aspect, it is contemplated that the center points 48 of neighboring perforations 46 can be spaced apart by a distance 49 ranging from about 0.35 mm to about 10 mm.

In exemplary aspects, and with reference to FIGS. 5A-7B, the disclosed support assembly (base 30 and cover 60) can be provided as part of a membrane product package 100. In these aspects, in addition to the support assembly, the membrane product package 100 can comprise a membrane 20 positioned in an operative position between the product receiving portion 40 of the base 30 and the cover 60 (relative to the vertical axis 34). As further disclosed herein, the membrane 20 can have an upper surface 26 and an opposed lower surface 28. It is contemplated that the membrane 20 can be positioned in engagement with at least a portion of the top surface 42 of the product receiving portion 40 of the base 30 and at least a portion of the bottom surface 66 of the cover 60.

In one aspect, the lower surface 28 of the membrane 20 can be attached to the top surface 42 of the product receiving portion 40 of the base 30 at least one attachment point 22. Optionally, in exemplary aspects, the lower surface 28 of the membrane 20 can be attached to the top surface 42 of the product receiving portion 40 of the base 30 at least three attachment points 22. Optionally, in further exemplary aspects, the lower surface 28 of the membrane 20 can be attached to the top surface 42 of the product receiving portion 40 of the base 30 at least five attachment points 22. Optionally, it is contemplated that the attachment points 22 can be cauterization points (where the product receiving portion 40 and the membrane 20 are cauterized together).

In one aspect, the cover 60 can be attached to the upper surface 26 of the membrane 20 at least one attachment point 24. Optionally, in exemplary aspects, the cover 60 can be attached to the upper surface 26 of the membrane 20 at least two attachment points 24. Optionally, in further exemplary aspects, the cover 60 can be attached to the upper surface 26 of the membrane 20 at least three attachment points 24. Optionally, it is contemplated that the attachment points 24 can be cauterization points (where the cover 60 and the membrane 20 are cauterized together).

Optionally, at least one attachment point 24 where the cover 60 is attached to the membrane 20 can overlie and/or substantially correspond to an attachment point 22 where the product receiving portion 40 of the base 30 is attached to the membrane 20. At these attachment points, it is contemplated that the base 30, the membrane 20, and the cover 60 can be secured together.

In addition to, or alternatively to, the attachment of the membrane 20 to the product receiving portion 40 and/or the cover 60, the top surface of the product receiving portion of the base can be directly attached to the cover at least one attachment point. Optionally, in exemplary aspects, the top surface 42 of the product receiving portion 40 of the base 30 can be attached to the cover 60 at least three attachment points. In these arrangements, it is contemplated that the membrane can have a length and a width that are less than the longitudinal length and the width of the product receiving portion 40 and the cover 60 to thereby define a peripheral edge region around the membrane 20, and at least one attachment point (where the product receiving portion is directly attached to the cover) can be positioned in the peripheral edge region and spaced from an outer edge of the membrane.

In exemplary aspects, the membrane 20 can be a natural membrane, such as, for example and without limitation, a placental tissue product. Optionally, in one aspect, the membrane 20 can be a chorionic membrane product. Optionally, in a further aspect, the membrane can be an amniotic membrane product.

In further exemplary aspects, the membrane 20 can be a synthetic membrane.

In still further exemplary aspects, it is contemplated that the membrane 20 and the top surface 42 of the product receiving portion 40 of the base 30 can have sufficient surface traction to maintain the membrane in the operative position following removal of the cover 60 from the base.

In additional exemplary aspects, the membrane 20 and the top surface 42 of the product receiving portion 40 of the base 30 can have a first surface traction. In these aspects, it is contemplated that the membrane 20 and the cover 60 can have a second surface traction that is lower than (less than) the first surface traction.

In exemplary aspects, and with reference to FIGS. 5A-5C, a method of producing a membrane product package as disclosed herein is provided. In these aspects, the method can comprise positioning a membrane in an operative position between the product receiving portion of the base and the cover of the support assembly. In these aspects, the membrane can be positioned in engagement with at least a portion of the top surface of the product receiving portion of the base and at least a portion of the bottom surface of the cover.

Optionally, the step of positioning the membrane in the operative position can comprise attaching the membrane to the top surface of the product receiving portion at a plurality of attachment points as disclosed herein. It is further contemplated that the step of positioning the membrane in the operative position can further comprise attaching the membrane to the cover at a plurality of attachments points as disclosed herein.

Optionally, in further aspects, the method can further comprise positioning the base, the membrane, and the cover within a cryopreservation solution. In these aspects, when the traction-creating feature of the product receiving portion of the base comprises a plurality of perforations as disclosed herein, the plurality of perforations can provide contact between the membrane and the cryopreservation solution sufficient to cryopreserve the membrane.

In additional exemplary aspects, a method of applying a membrane is disclosed. In these aspects, the method can comprise removing the cover from a membrane product package as disclosed herein to expose a top surface of the membrane. In another aspect, the method can further comprise disengaging the membrane from the top surface of the product receiving portion of the base. In a further aspect, the method can further comprise selectively applying the membrane to a desired location on a human or animal patient.

In further exemplary aspects, a kit for repairing a tissue defect is disclosed. In these aspects, the kit can comprise a membrane product package 100 as disclosed herein. In additional optional aspects, the kit can further comprise a container (e.g., a bag) that encloses the membrane product package. In these aspects, the container can be selectively opened to provide access to the membrane product package. In further optional aspects, the kit can further comprise instructions for applying the membrane of the membrane product package to repair the tissue defect. In still further optional aspects, the kit can further comprise a cryopreservation solution. Optionally, in other aspects, the kit can further comprise a basin configured to receive the membrane product package. In these aspects, it is contemplated that the basin can serve as a wash basin and/or thawing basin for the membrane product package. In still another aspect, the kit can optionally comprise scissors. In yet another optional aspect, the kit can comprise tweezers.

Further exemplary aspects of the disclosed concepts are provided in the following sections of the specification.

The Base a. Product Membrane Receiving Portion

As shown in FIGS. 1A, 2A, 3A, 5A-5C, 6A, 7A, and 9, the base 30 of the presently described technology comprises at least one receiving portion 40. The receiving portion 40 is capable of receiving a biological product, material, or composition 20. Such materials or compositions may include, for example, membranes, tissues, graft materials, and the like. Throughout the remainder of the specification and appended claims, the biological product will generally be referred to as a "membrane," and the receiving portion 40 shall be referred to interchangeably as either the "product receiving portion" or the "membrane receiving portion." It should be appreciated by those skilled in the art, however, that the term encompasses and contemplates the receipt and engagement of other biological materials such as tissues, other biological materials and grafts. The membrane receiving portion 40 is a portion of the base 30 (of the present technology) that contacts the membrane 20. The membrane receiving portion 40 of the present technology also can comprise at least one traction-creating feature. As further disclosed herein, the traction-creating feature provides a surface which, when in contact with the membrane 20, provides sufficient surface traction such that the membrane remains sufficiently but temporarily attached to the base 30 and prevents, for example, curling or detachment of the membrane during manufacture, storage, transport and handling prior to final removal from the packaging or packaging system and application to an end user or for an end use application (e.g., wound treatment, diagnostic testing or experimental/analytical laboratory usages). Thus, the traction-creating feature (e.g., a structured surface) provides sufficient support, attachment/connection and/or stabilization of the membrane 20 in conjunction with the base 30 when applied thereto. This is unexpected since the packaging device, composition, article of manufacture or system of the present technology itself (e.g., the support assembly disclosed herein), not the membrane, tissue or graft material, provides such outcomes, especially during each of the phases of preparing, storing, transporting, handling, and administering of the end product. It is also unexpected that the presently described technology can provide such outcomes while still allowing the end user to size, shape and finally apply the end product to the patient (human or animal) in a convenient manner without significant waste, destruction, damage, injury, or other negative outcome to the membrane to be applied.

As further described herein, the traction-creating features may be any suitable surface feature that provides the necessary surface traction when in contact with the membrane, tissue, biological material or graft material. The surface traction necessary to maintain contact with the membrane, tissue, or graft (or other biological material to be delivered) will depend upon the composition of the membrane, tissue, graft or other biological material to be applied, temporarily affixed or attached in some non-permanent manner to the membrane receiving portion 40. The type of material used to form or make the base 30 will also affect the surface traction necessary to maintain contact between the membrane, tissue, graft or other biological material with the traction-creating feature of the membrane receiving portion of the base. Thus, it should be appreciated by those skilled in the art that the surface traction depends on a number of factors, including the type of base material selected, the traction-creating features of the membrane receiving portion (including, for example, the perforation, channel, groove, indentation pattern, or other pattern or surface type selected/desired), and the type of membrane. In at least one embodiment of the present technology, a sufficient surface traction is characterized by a package (i.e., a device, a composition, an article of manufacture) or packaging system of the present technology having the following features: 1) at least one membrane that does not spontaneously detach from the base (or a selected portion, segment or part of the base) when submerged in a medium (e.g., a biological medium, including a biological solution) and 2) the ability of the membrane to slide from the base without ripping, tearing or damage to the membrane when removed from the packaging or packaging system and then subsequently applied to the wound or tissue defect of the human or animal to be treated.

Other suitable methods of testing surface traction sufficient for the purposes of practicing the present technology may be determined by equipment and methodology known conventionally. For example, a sufficient surface traction can be determined instrumentally via an Instron measurement device commercially available from Instron, Incorporated of Norwood, Mass. (a manufacturer of surface traction testing equipment designed to evaluate the mechanical properties of materials and components (www.instron.us/)). Surface traction in some instances is also known as sliding frictional force. Sliding frictional force is understood and can be determined by one skilled in the art, for example, see *Sliding Friction: Physical Principles and Applications* (NanoScience and Technology) by Bo Persson (Jun. 21, 2000) $2^{nd}$ edition, Springer (ISBN-10: 3540671927|ISBN-13: 978-3540671923), and Advances in Soft Matter Mechanics by Shaofan Li, and Bohua Sun (2012), (ISBN: 978-3-642-19372-9 (Print) 978-3-642-19373-6 (Online)), incorporated by reference in their entireties.

Traction-creating features (e.g., structured surfaces) can include, but are not limited to, for example, a rough surface (e.g., an uneven surface, a scratched surface, and the like), a surface comprising a plurality of perforations or porations, a surface comprising a plurality of channels (a channeled surface), a surface comprising a plurality of grooves (a grooved surface), or a surface comprising a plurality of indentations (an indented surface), among others. Combinations of such surfaces can also be utilized. In some instances, the traction-creating features comprise at least one perforation, at least one channel, at least one groove, at least one indentation, and in some instances, the at least one perforation, at least one channel, at least one groove or at least one indentation is a complex pattern or design. In one exemplary aspect, the traction-creating feature can comprise a sandpaper-roughened surface.

Further, a variety of patterns, designs or shapes of various traction-creating features (e.g., structured surfaces) can also be utilized in the practice of the presently described technology. For example, the traction-creating feature (e.g., structured surface) may be a circular pattern of perforations, alternatively, a square pattern of perforations and the like. Further designs, shapes, and patterns suitable for use in the practice of the present technology are illustrated in FIGS. 1A-9. It should be appreciated by those skilled in the art that any pattern, design or shape may be utilized as long as a sufficient surface traction between the traction-creating feature and the membrane, tissue, graft or other biological material can be achieved such that the membrane, tissue, graft, or other biological material is stable and supported during manufacture, storage, transport and handling prior to final application of the membrane to the end user (or for its use in an end application such as diagnostic or analytical testing). Yet, the sufficient surface traction (and associated attraction, affinity, and/or adhesion) is only temporary such that the end user can remove the membrane, tissue, graft, or other biological material for final application to the human or animal patient (or for final end application usage) without significant negative outcomes such as curling, self-adherence, damage, injury and the like. In some embodiments of the present technology, the traction-creating feature (e.g., structured surface) can be irregular, continuous, discontinuous, symmetrical, dissymmetrical in design, shape or pattern, or comprise a combination of different types of traction-creating features (e.g., structured surfaces).

During storage, such as cryopreservation storage, it should be appreciated by those skilled in the art that the traction-creating feature (e.g., structured surface) of the membrane receiving portion provides enough or sufficient surface traction such that the membrane is able to temporarily adhere or remain attached or connected to the base and is not significantly dislodged from the base when a cryopreservation solution is introduced into the packaging device, composition, article of manufacture or system of the present technology. It has been surprisingly found that the present technology allows the membrane, tissue, graft or other biological material to remain temporarily adhered, attached or connected to the membrane receiving proportion sufficient to withstand shear fluid force that is typically produced when a cryopreservation solution or other solution or liquid material is introduced into the packaging device, article of manufacture, composition, or system. The fluid may be introduced, for example, into a bag or other suitable container that can be part of the device, composition, article of manufacture, or system of the present technology that may hold the base/membrane/cover configuration therein or thereupon. Again, it should be appreciated by those skilled in the art that the present technology via the traction-creating feature (e.g., structured surface) of the membrane receiving portion of the base (alone or alternatively in combination or further communication with the cover), provides sufficient surface traction with the membrane, tissue, graft or other biological material to stabilize, support, and to temporarily hold in place that membrane while withstanding freezing procedures, shipping, storage, handling and thawing procedures prior to final application to a wound or tissue defect.

The membrane receiving portion of the present technology may span the entire length of the base or may span only a portion, section, part or segment of the base. In some aspects, for example, the membrane receiving portion can span at least 30% of the length of the base. In other aspects, the membrane receiving portion can span at least 40% of the length of the base. In additional aspects, the membrane receiving portion can span at least 50% of the length of the base 30. In still further exemplary aspects, the membrane receiving portion can span at least 60% of the length of the base 30. In still further exemplary aspects, the membrane receiving portion can span at least 70% of the length of the base 30. In still further exemplary aspects, the membrane receiving portion can span at least 80% of the length of the base 30. In still further exemplary aspects, the membrane receiving portion can span at least 90% of the length of the base 30. In still further exemplary aspects, the membrane receiving portion can span at least 95% of the length of the base 30. In some embodiments, the membrane receiving portion spans about 95% of the length of the base. In other embodiments, for example, the membrane receiving portion spans about 30%, about 35%, about 40%, about 45%, about 50%, about 55%, about 60%, about 65%, about 70%, about 75%, about 80%, about 85%, about 90%, about 95%, about 98%, about 99%, or about 100% of the length of the base, and it should be appreciated that such spans can include increments and percentages in between (for example, 70%, 71%, 71.5%, 72%, 72.5%, 73%, among others).

The term "plurality" when used to describe a plurality of perforations, a plurality of channels, a plurality of grooves, or a plurality of indentations, for example, refers to a sufficient number of such perforations, channels, grooves, indentations and the like being distributed throughout the membrane receiving portion so as to provide a sufficient tension or surface traction for the graft, tissue, membrane or other biological material to temporarily adhere, connect or attach to the base and withstand the processing and handling during manufacture, transport, storage, handling and final application to a wound or tissue defect.

b. Perforation of the Membrane Receiving Portion

In some embodiments of the present technology, and with reference to FIGS. 1A, 2A, 3A, and 5A-5C, the membrane receiving portion 40 comprises a plurality of perforations 46 and/or porations. In some embodiments, the membrane receiving portion 40 may comprise at least one perforation 46. The at least one perforation may be a complex pattern or design. Optionally, each perforation 46 can be a small hole within a material (e.g., the membrane receiving portion of the base). It is contemplated that the perforations 46 can be formed by any suitable means in the art. Continuous perforated or microperforated sheets for use in the practice of the present technology may be prepared by any conventional method known in the art utilizing a substrate sufficient and consistent with the practice and intentions of the presently described technology to temporarily adhere, attach, or connect the membrane 20 while providing support as well. Suitable means for perforating the base 30 (or membrane receiving portion 40 of the base) can include, but are not limited to, mechanical perforation devices such as suitably arranged punching machines, thermal or ultraviolet lasers operating in a desired frequency band, rotary pinned perforation rollers, a die and punch set, a vacuum, a needle or water jet perforation device or system, hot pins, an embossing device or system and any combinations thereof, among others.

The plurality of perforations (or porations) 46 may also comprise a shape, design, or pattern or may be randomly orientated within the membrane receiving portion 40 of the base 30. In still further embodiments, the plurality of perforations 46 are evenly distributed across the membrane receiving portion 40. The perforations 46 may be simply ordered or may be arranged according to complex sequences. The pattern of the plurality of perforations 46 may comprise, for example, a grid pattern (e.g., a series of rows and columns). In some embodiments of the present technology, the size of each perforation 46 can be from about 0.1 mm to about 5 mm. Suitably, the perforations 46 can have a diameter (maximum width) of about 0.2 mm, about 0.3 mm, about 0.4 mm, about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2.0 mm, about 2.1 mm, about 2.2 mm, about 2.3 mm, about 2.4 mm, about 2.5 mm, about 2.6 mm, about 2.7 mm, about 2.8 mm, about 2.9 mm, about 3.0 mm, 3.1 mm, about 3.2 mm, about 3.3 mm, about 3.4 mm, about 3.5 mm, about 3.6 mm, about 3.7 mm, about 3.8 mm, about 3.9 mm, about 4.0 mm, about 4.1 mm, about 4.2 mm, about 4.3 mm, about 4.4 mm, about 4.5 mm, about 4.6 mm, about 4.7 mm, 4.8 mm, about 4.9 mm and about 5.0 mm and any increments between, including increments from between about 0.01 mm to about 0.1 mm. In further aspects and embodiments of the present technology, the perforation size can preferably range from about 0.1 mm to about 20.3 mm, and spacing can be about 0.35 mm to about 20 mm center to center. Optionally, in some exemplary aspects, the diameter of at least one perforation 46 can be different (less than or greater than) the diameter of at least one other perforation of the plurality of perforations.

The number and size of the perforations 46 depends upon the material or substrate of which the membrane receiving portion 46 is made from, the type of membrane 20, tissue, graft or other biological material adhered, attached, connected or associated (all temporarily) with the membrane receiving portion, and the surface traction that is sufficient to maintain the membrane, tissue, graft and/or other biological material temporarily on, onto, connected to, attached to, adhered to and the like to the base 30 during processing, storing, transporting, and handling. Additionally, the perforations (or porations) 46 may be any geometrical or non-geometrical shape. Suitable shapes include, but are not limited to, circular, oval, rectangular, square, diamond, trapezoidal, star, hexagonal, octagonal, semi-circular, crescent, ellipse or a combination thereof. Perforations (or porations) 46 may also be a section or part of a shape, such as a half star or half crescent. It should be understood by those skilled in the art that one or more shapes may be used in any combination as well.

The center-to-center distance 49 between adjacent (neighboring) perforations (or porations) 46 on the base 30 (or membrane receiving portion 40 of the base) depends upon the size and number of perforations (or porations) 46 that can be distributed throughout the area selected (for example, the size of the membrane receiving portion) and the overall selected size of the base, itself. The size and number of perforations (or porations) 46 permissible in the base 30 (or membrane receiving portion 40 of the base), in turn, depend upon the effect of the same upon the physical properties of the base, the cover 60, and the stabilizing, temporarily connective and protective functions served by the base and structure of the perforations with respect to the associated membrane 20, tissue, graft and/or other biological material(s). For example, the distance 49 between perforations 46 as measured from the center of one perforation to the center of another perforation may be from about 0.3 to about 10 mm, alternatively from about 0.35 mm to about 10 mm, alternatively from about 0.35 mm to about 5 mm, alternatively from about 1 mm to about 5 mm, alternatively from about 4 mm to about 10 mm, and any increments and distances in between, including increments from about 0.01 mm to about 0.1 mm. Preferably, the distance 49 between perforations (or porations) 46 is from about 1 mm to about 10 mm, more preferably about 3 mm to about 5 mm, such as 3 mm or 4 mm.

While not wanting to be bound by any particular theory, it has been observed and discovered in the practice of the present technology that the smaller the membrane 20 (tissue, graft, or other biological material(s)) to be attached to the base 30 (or membrane receiving portion 40 of the base), the smaller the perforations (or porations) 46 can be within the base (or membrane receiving portion of the base). Conversely, the larger the membrane 20 to be attached to the base 30 (or membrane receiving portion 40 of the base), larger perforations (or porations) 46 can be utilized and the farther apart the perforations (or porations) can be spaced as well. For example, for a 7.5 cm×15 cm (7.5 cm length×15 cm width) membrane, the perforations may be about 5 mm in diameter and about 10 mm apart (as measured center to center). For a membrane that is approximately 1.5 cm×2 cm, the perforations may be about 1 mm diameter and about 4 mm apart center to center. In some embodiments of the present technology, for a membrane that is approximately 5 cm×5 cm or 3 cm×4 cm, the perforations may be about 1 mm diameter and about 4 mm apart center to center. In other embodiments, for an approximately 2 cm×3 cm membrane, the perforations may be about 1 mm diameter and about 3 mm apart center to center. It should be appreciated by those skilled in the art that such examples are for illustrative purposes only and are not to be considered exhaustive. In some instances, not to be bound by any particular theory, for membrane sizes over 100 cm$^2$ the size of perforations may be increased up to five fold and the distance between the perforations may be increased by 2-3 fold.

Preferably, the method of forming perforations (or porations) should not create microparticles or other impurities or contaminants (or pollutants) that are permanently stained on the base and cannot be removed, or would otherwise be detrimental to the membrane. Further, the perforated (or porated) base (or membrane receiving portion thereof) should be free of oil or other chemicals, materials, impurities, pollutants, contaminants or substances that may interfere with the performance of the base and the membrane receiving portion according to the practice of the present technology, or would otherwise not be biocompatible or would be detrimental to the membrane. Moreover, the base and membrane receiving portion (however modified, for example, via perforating, grooving, channeling, etc.) should be able to maintain a sufficient cleanliness to protect and/or maintain the cellular viability of the associated membrane, tissue, graft and/or other biological materials temporarily associated therewith, maintain integrity of the associated membrane, tissue, graft and/or other biological materials temporarily associated therewith, and/or provide safety for the human or animal being treated (e.g., comply with safety regulations). In doing so, a detrimental response by a patient to the membrane, tissue, graft and/or other biological material(s) can be reduced or prevented when provided to patients, (e.g., when applied to or transplanted on or within various areas of a patient(s) such as a wound or tissue defect).

c. Grooves/Channels/Indentations, Etc.

In some embodiments of the present technology, the membrane receiving portion 40 may comprise a plurality of grooves. In some embodiments, the membrane receiving portion 40 may comprise at least one groove, wherein in some instances, the at least one groove is a complex pattern or shape. The grooves can span the entire length of the membrane receiving portion or any segment, portion, or part thereof. The grooves may be discontinuous or continuous over the entire length or portion (or segment or part) of the membrane receiving portion of the base. The grooves can be orientated in parallel or in a perpendicular conformation, or a combination thereof. The grooves may be evenly distributed or randomly distributed over the respective length, segment, portion or part of the membrane receiving portion. The grooves should cover a sufficient area of the membrane receiving portion to provide a sufficient surface traction such that the membrane, tissue, graft and/or other biological material associated therewith temporarily adheres, connects, or attaches to the membrane receiving portion (or base) for purposes of stabilization, temporary connection and protection during manufacture, handling, storage, transport and final application or usage.

In other embodiments of the present technology, the membrane receiving portion 40 may comprise a plurality of channels. The channels may be discontinuous or continuous over the entire length of the membrane receiving portion, or alternatively a portion, part, or segment thereof. The channels may be evenly distributed or randomly over the membrane receiving portion. The channels can be orientated in a parallel conformation to one another, a perpendicular conformation to one another, or a combination thereof. The channels preferably cover a sufficient area of the membrane receiving portion of the base to provide sufficient surface traction such that the membrane temporarily adheres, connects or attaches to the membrane receiving portion during manufacturing, handling, storage and final application or usage.

In still other embodiments, the membrane receiving portion 40 of the present technology can comprise a plurality of indentations. The indentations may be evenly distributed over the entire length, portion or segment of the membrane receiving portion of the base. The channels may be randomly or evenly distributed over the entire length, portion or segment of the membrane receiving portion. The indentations may also be arranged in rows and other patterns, designs or configurations. The rows may be parallel or intersecting over the entire (or alternatively a portion, part, or segment of the) length, of the membrane receiving portion of the base. The indentations should cover a sufficient area of the membrane receiving portion of the base to provide sufficient surface traction such that a membrane, tissue, graft, or other biological material(s) sufficiently but temporarily adheres, connects or attaches to the base during manufacturing, handling, storage, transit and final application or usage.

d. The Membrane Receiving Portion Surface

Figure 9:
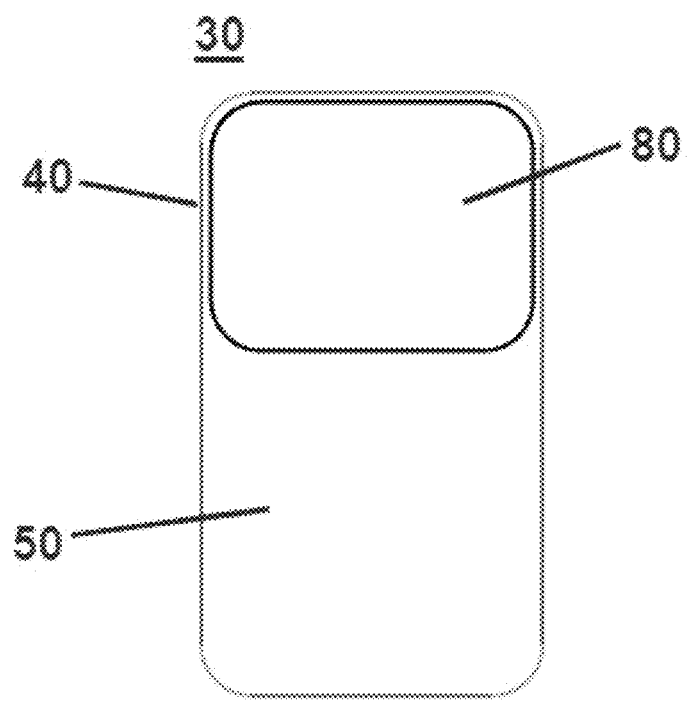
FIG. 9 is an isolated top view of a product receiving portion having a rough surface as disclosed herein.

In some embodiments of the present technology, and with reference to FIG. 9, the membrane receiving portion 40 of the base is a rough surface 80, preferably a rough plastic surface. However, it should be appreciated that other materials suitable for use to practice the presently described technology are also envisaged. Suitable means of making a rough surface include, but are not limited to, sanding, chemical alteration, 3-D printing, abrasive blasting, and other methods known to one skilled in the art. The rough surface 80 should provide a sufficient surface traction such that the membrane, tissue, graft, or other biological material(s) temporarily adheres, connects, or attaches to the membrane receiving portion of the base during manufacturing, handling, storage, transit and final application or usage, but not too strongly so as to not be able to be easily removed and applied (e.g., to a wound or tissue defect or for use in a further procedure).

In other embodiments, the membrane receiving portion 40 may exhibit a scratched surface. Again, the scratched surface should provide a sufficient surface traction such that the membrane, tissue, graft, or other biological material(s) temporarily adheres, connects, or attaches to the membrane receiving portion of the base during handling, storage, transit and application, but not too strongly so as to not be able to be easily removed and applied (e.g., to a wound or tissue defect or for use in a further procedure).

e. Handling Portion

In some aspects and embodiments of the present technology, and with reference to FIGS. 1A, 2A, 3A, 5A-5C, 6A, 7A, and 9, the base 30 further comprises at least one handling portion 50. The handling portion 50 may be, for example, adjacent to the membrane receiving portion 40. The handling portion 50 provides a region of the device, system, article of manufacture, or composition of the present technology that can be handled or operated by an individual without causing damage, injury to or significant waste, disorientation, or negative outcomes to the membrane 20 (tissue, graft, or biological material(s)) applied thereto. This reduces direct contact with the membrane 20 and a handler, which reduces damage to the membrane (among other things) and maintains, in the case of living membranes, cellular viability, and other attendant beneficial biological properties and functions when applied to a patient or utilized in other therapeutic, diagnostic, analytical and/or experimental laboratory manners.

In still further embodiments, and with reference to FIGS. 6A and 7A, the handling portion 50 can also contain a marker, label or designation 55 for orientation and/or application. This allows for the indication of the directionality, spatial arrangement or proper application of a membrane 20 (e.g., tissue, graft, or other biological materials) temporarily applied to the membrane receiving portion 40 of the base 50, which can be maintained throughout preparation, cryopreservation, storage, transport, thawing and final application to a patient or other usage. The marker 55 for orientation may be any symbol that can indicate a proper orientation, proper application or usage, and/or directionality. For example, the marker 55 can be a name, a trade name for the packaging product (kit or system), an arrow, at least one word or a letter, a directional symbol, or other suitable alternatives. To illustrate, suitable letters that require orientation, for example, include but are not limited to B, C, D, E, F, G, J, K, N, P, Q, R, S, and/or Z. To further illustrate, suitable orientation markers 55 may be the name of the product, for example Grafix PRIME® or Grafix CORE® owned by Osiris Therapeutics, Inc. of Columbia, Md. In other embodiments, the marker 55 may be a word or phrase, for example "top," "this side up," face," "forward," "product," "handle side", "keep this side up." One of skill in the art shall appreciate additional alternatives that can provide the orientation, proper application, and/or directionality of the device, composition, article of manufacture, or system of the present technology. In some embodiments, the label or marking 55 may be a colored letter, square, block or edge. In doing so, the device, composition, article of manufacture, or system of the present technology provides the advantage of informing the handler of the proper orientation placement of at least one membrane 20 (e.g., tissue, graft, or other biological material) on, onto, or upon the membrane receiving portion 40 of the base 30. Further, the marker 55 for orientation also provides information to a handler (e.g., a health care provider) regarding the proper orientation of the device, composition, article of manufacture, or system of the present technology (e.g., the support assembly or membrane product package 100 disclosed herein) prior to the membrane, tissue, graft, or other biological material(s) being applied to the patient. Thus, it should be appreciated by those skilled in the art that any shape, symbol, color, design, pattern and the like may be utilized and are envisaged in the practice of this aspect and embodiments of the present technology.

Optionally, in additional embodiments, the cover 60 comprises at least one handling portion. The handling portion of the cover 60 may also contain a marker for orientation and/or labeling of the product as described herein. The handling portion of the cover 60 may also be used for removal of the cover) during the end application process (e.g., to a patient or usage during a diagnostic procedure, laboratory analysis or some other usage). In some of these embodiments, the handling portion can be a grip. The grip may be used to remove the cover that is temporarily adhered, connected or attached from the membrane, tissue, graft, or other biological material(s) and base.

In other embodiments, both the cover 60 and the base 30 both separately comprise at least one handling portion or can jointly form at least one handling portion. In still further embodiments, the base 30 may comprise a first handling portion while the cover 60 may comprise a second handling portion that may operate separately or may work cooperatively with the first handling portion. In other embodiments, the first handling portion and the second handling portion are in communication with each other. The communication is preferably temporary but sufficient to maintain communication during manufacture, handling, transport and prior to final application or usage. For example, in some embodiments, the second handling portion can overlap at least a part, portion, or segment of the first handling portion.

Additionally, it should also be appreciated that the respective handling portion (of the base 30 or the cover 60) can be the entire width of the cover and/or the base. Alternatively, the handling portion may comprise only a portion, segment, or part of the width of the cover and/or base. A portion, segment, or part of the width may be about 10%, about 20%, about 30%, about 40%, about 50%, about 60%, about 70%, about 80%, about 90%, about 95% of the width, and any percentage or width in between. The handling portion should be sufficiently sized so as to provide a region of the cover and/or base to allow a handler to safely handle the device, composition, article of manufacture or system of the present technology without causing injury or damage to the membrane, tissue, graft, or other biological material(s) associated therewith. Further, the handling portion should be sufficiently sized so as to provide ease of handling by the handler. Moreover, the handling portion should be sufficiently shaped so as to provide easy of use while providing a more comfortable handling, such as through the prevention of cuts upon the handlers fingers during handling that can result if the edges of the handling portion are not smoothed (e.g., rounded or sanded, etc.).

In some embodiments of the present technology, the handling portion is from about 1 cm to about 5 cm wide and the same length as the membrane receiving portion 40 of the base 30. Sizing of the handling portion depends on the size of the membrane receiving portion of the base, and the handle portion in some optional embodiments does not exceed the size of the membrane receiving portion of the base. In other embodiments, the handling portion is about 1 cm wide, preferably about 2 cm wide, alternatively about 2.5 cm wide, alternatively about 3 cm wide, and spans the entire length or a portion, part, or segment of the entire length of the membrane receiving portion. In still further embodiments, the handling portion is preferably at least about 1 cm wide.

The Cover

With reference to FIGS. 1B, 2B, 3B, 4B, 5A, 5C, 6B, and 7B, the cover 60 of the compositions, devices, articles of manufacture or systems of the present technology (e.g., the support assembly and the membrane product package 100) can optionally be the same size as the base 30. Alternatively, in other embodiments, the cover 60 is substantially the same size as the membrane receiving portion 40 of the base 30. Preferably, the cover 60 is of a sufficient size to protect a membrane 20 (e.g., tissue, graft or other biological material(s) that is temporarily attached, connected, or adhered to the cover and/or the membrane receiving portion of the base) from shear forces and stresses produced or faced during processing, storage, transport, handling and final application or usage. In the various embodiments of the present technology, the cover 60 can optionally be a single piece of suitable biocompatible substrate. In some embodiments, the substrate is a biocompatible plastic, biopolymer, biocopolymer or other biocompatible material that does not significantly injure, damage, contaminate or otherwise harm the associated membrane of the present technology.

Shape/Size/Make-Up of the Cover and Base

In some embodiments of the present technology, the base 30 can exhibit a shape that comprises non-sharp corners 45, 52. Optionally, the corners of the base 30 can be rounded. In still further embodiments, the cover 60 can comprise non-sharp corners 68. In some preferred embodiments, the corners 45, 52, 68 of the cover and/or base are rounded. Non-sharp corners are preferred for safety and handling of the device, system, article of manufacture, or composition of the present technology during manufacturing, storage, transport, or application/usage, and also to prevent tearing or puncturing of the temporarily associated membrane, tissue, graft, or other biological material(s) during removal from the base and/or cover. It should be appreciated that the base and cover may be of any desired geometrical shape. In some preferred embodiments, the base and cover are squares or rectangles, preferably squares or rectangles with rounded corners. However, it is further contemplated that the cover and/or base can have a round shape (e.g., a circular or elliptical shape).

It should also be appreciated by those skilled in the art that the device, article of manufacture, composition, or system (e.g., the support assembly or the membrane product package 100) can exhibit a varying size. In some embodiments, the size of the device, article of manufacture, composition or system can be a customizable size for a particular application which is chosen by the manufacturer or the handler prior to end application or usage. For example, in some embodiments, the size (longitudinal length×width) can be about 1 cm×1 cm, about 1.5 cm×2 cm, about 1.5 cm×1.5 cm, about 2 cm×2 cm, about 2.5 cm×2.5 cm, about 2 cm×3 cm, about 2 cm×4 cm, about 2 cm×5 cm, about 3 cm×4 cm, about 3 cm×5 cm, about 5 cm×5 cm, about 4 cm×5 cm, about 5 cm×7 cm, about 1.5 cm×3.5 cm, about 7.5 cm×15 cm, about 9.5 cm×15 cm, about 7.5 cm×17 cm, and other sizes and ranges there between.

In a variety of embodiments of the present technology, the base and/or cover are each individually made of a singular piece of plastic, preferably a biocompatible plastic. Alternatively, in other embodiments, the base and the cover can be made collectively from a singular piece of plastic, again preferably a biocompatible plastic. For example, in such embodiments, the singular piece of plastic can be folded such that the base and the cover are formed and interact with one another, preferably temporarily. Further, the first side of the base can be continuous with a first side of the cover. Thus, a membrane, tissue, graft, or other biological material may be placed between the first side of the base and the first side of the cover, wherein a second side of the cover is facing externally to the membrane. In still further embodiments, the base and the cover may each be or collectively be a single piece of biocompatible plastic produced by 3-D printing. In other embodiments, the single piece of plastic for each of the base and cover may have latches, handles, or other forms of attachment and connection that can connect the base to the cover and vice versa. For the example, the first side of the base can be fixedly attached or connected to the first side of the cover via two interlocking or connecting handles or a hook and latch enclosure system, for example.

In further embodiments, the base and the cover can be made of, for example, at least two substrates. In some embodiments, the substrates are two of the same or different biocompatible plastics. In other embodiments, the base and the cover are comprised of the same type of substrate while in other embodiments the cover and base are made from different substrates. Thus, one of ordinary skill in the art will appreciate that a variety of substrates can be utilized to make the various parts of the presently described technology as long as the sufficient characteristics of the components allow for the support, stabilization, temporary connection or attachment of the selected membrane thereto with a sufficient surface traction to prevent injury, damage, detachment of the membrane during manufacturing, storage, transporting, handling and end application or usage. To illustrate, in still further embodiments, the base and the cover are made from different types of substrates, with the different types of substrates being different types of biocompatible plastics, biopolymers, biocopolymers, or other biocompatible materials. More particularly different types of biocompatible plastics, for example, may be a single plastic composition, a multiple-composition plastic, or layers of a biocompatible plastic(s) selected. As should be appreciated by those skilled in the art, further alternatives are also envisaged.

Communication Between the Base and the Cover

In some embodiments of the present technology, and with reference to FIGS. 5A-7B, the device, article of manufacture, system and/or composition comprises a base 30, a cover 60, and at least one location (attachment point 22, 24) in which the base and the cover are in operative communication, which can be direct communication (e.g., temporary direct communication) or indirect communication (e.g., temporary indirect communication) through a membrane 20 as disclosed herein. In other embodiments, the base 30 and cover 60 are in sufficiently close proximity and are attached to one another and/or to a membrane 20 by temporary or removable attachments or connections. Suitable methods of communication can include, but are not limited to, heat sealing, cauterization, welding, ultrasonic welding, a biocompatible adhesive (preferably an adhesive suitable for use with biological and/or cellular materials), use of a laser, use of an interconnecting means, crimping (by heat or mechanically by pressure), crunching, stapling, or clamping, among others. Preferably, the attachment or connections include, but are not limited to, at least one discrete cauterization point, at least one latch, or at least one ultrasonic welding point by which the cover, membrane (tissue, graft, or other biological material(s)) and base are temporarily connected or attached. To illustrate, a sufficient number of cauterization points (attachment points 24) can be utilized to attach the membrane 20 (tissue, graft, or other biological material(s)) to the cover 60 and a sufficient number of cauterization points (attachment points 22) can be utilized to attach the membrane 20 (tissue, graft, or other biological material(s)) to the base 30 as well. Optionally, when the membrane 20 has a smaller length and/or width than the cover 60 and the membrane receiving portion 40 of the base 30, a sufficient number of cauterization points (or other attachment points) can be utilized to attach the cover directly to the membrane receiving portion, with the membrane being inwardly spaced from such attachment points. Thus, it is contemplated that the membrane 20 can be secured between the cover 60 and the base 30 without directly attaching the cover and/or the base to the membrane at an attachment point. It should be appreciated by those skilled in the art that any number of cauterization points or other temporary attachments between the membrane (tissue, graft, or other biological material(s)) and the cover and/or base can be used in the practice of the present technology. Further, the level of temporary attachment can be varied depending upon the type of material used to make the cover and/or base as well as the type, size, depth (among other variables) of the membrane, tissue, graft or other biological material(s) temporarily attached, connected, or applied thereto (i.e., temporarily attached or connected to the cover, the base or both). In exemplary aspects, the attachment points (e.g., cauterization points) can be generally positioned in the outer edge portions of the cover 60, base 30, and membrane 20, thereby minimizing functional damage to these components.

Focusing upon the connective relationship between the cover and base, in some additional embodiments, the at least one connection or attachment location in which the base and the cover are in communication with one another (inclusive or not inclusive of the membrane, tissue, graft, or other biological material(s)) comprises one or more interconnecting means or connective devices, connectors and the like. For example, the communication can be a female connector and a male connector, wherein the male connector secures into the female connector to provide a suitable attachment between the base and the cover. The suitable connection may be disrupted by sufficient force to remove the male connector from the female connector. In other embodiments, the female connector can comprise an indentation while the male connector can comprise a protrusion in a shape suitable to fit or connect within the indentation. Again, these examples are for illustrative purposes only and are not an exhaustive exemplary listing.

It should also be appreciated that the number of temporary connection or attachment locations or points between the base and the cover, as well as the base and/or cover and the membrane (tissue, graft, or other biological material(s)) depends on the manufacturing processes and handling processes utilized as well as the type of membrane (tissue, graft, or other biological material(s)) selected. However, in accordance with the practice of the present technology, the number of temporary connection or attachment locations must provide sufficient traction, adhesion, attachment or connection to withstand multiple stresses experienced during processing, storage, transport, handling and usage/application. For example, the number of connection or attachment locations must be sufficient to ensure the associated membrane, tissue, graft, or other biological material(s) remains temporarily attached, adhered, or connected to the cover and/or base while enduring fluid shear force created during manufacturing of the present technology or its packaging, during cryopreservation and thawing and also during transit should the cryomedium potentially thaw prematurely, shift, move or otherwise develop shear forces and the like that could potentially affect the membrane interacting therewith.

Additionally, as further described herein, the number of connection or attachment locations of the present technology (i.e., those of the cover and the base as well as those of the cover and/or base to the membrane, tissue, graft, or other biological material(s)) must be able to withstand storage (including, for example, cryopreservation (as well as the step of the inclusion or addition of a cryopreservation medium provided during the manufacturing or storage process)). Moreover, the connection or attachment locations also are preferably capable of withstanding temperature changes, including temperature changes ranging from 60° C. to −196° C. (+5° C.), alternatively from about 80° C. to about −196° C.±5° C. (alternatively from about 40° C. to about −196° C. (+5° C.) for a membrane or biological material containing viable cells), among others. Conversely, the connection or attachment locations and/or points of the present technology are also preferably capable of withstanding the temperature variances and other forces associated with thawing of the device, composition, article of manufacture, or system of the present technology. For example, such connection or attachment locations preferably are maintained when the device, composition, article of manufacture, or system is unthawed from about −80° C. or −196° C. (+5° C.) to about room temperature. (20° C. to about 25° C.) or about 40° C. (+5° C.). Further, the connection or attachment locations and/or points of the present technology described herein also preferably are capable of withstanding additional handling prior to final application or usage such as during washing of the device, composition, article of manufacture, or system during the performance of a thawing procedure.

The number of connection or attachment locations will depend upon the connection or attachment properties of the membrane, tissue, graft or other biological material(s) utilized and the type of material (e.g., a plastic substrate selected) used to form the cover and/or the base. The number of connection or attachment locations should allow for easy removal of the cover without disturbing the further attachment or connection between the membrane, tissue, graft, or other biological material(s) and the base. Further, the connection(s) or attachment(s) between the base and the membrane (tissue, graft, or other biological material(s)) should also be easily broken without tearing or damaging the membrane (tissue, graft, or other biological material(s)).

Additionally, the connection(s) or attachment(s) between the base and/or the top and the membrane should be such that they do not contaminate, break-off, or pollute the membrane. Moreover, the connection(s) or attachment(s) between the base and the membrane (tissue, graft, or other biological material(s)) should allow a handler (e.g., a health care provider) to easily remove and apply the membrane, tissue, graft or other biological material(s) to an end user (e.g., a patient having a wound or tissue defect) or for use in an end use application.

In further embodiments of the present technology, the connection or attachment locations can be a latch or latch system. A latch may be any mechanical fastener that is used to join two or more objects or surfaces together while allowing for the regular separation of the objects or surfaces so connected or attached. A latch may consist of a fastener that engages a catch, groove, hole, or suitable equivalent to temporarily affix or hold the base and the cover in close proximity. Suitable latching systems are known in the art. The latch may also consist of at least one flexible singular piece of substrate (e.g., a biocompatible plastic) that engages with a hole (or alternatively over the edge of) the base and/or cover to retain each so that they are in close proximity, preferably in a temporary fashion or manner. Finally, the at least one connection or attachment location for coupled communication between the base and the cover may also include discrete points or regions. In other embodiments, the at least one attachment or connection location may be at least one side or a portion of a side of the base and cover. In some embodiments, the coupled communication may be at least two sides (or portions of each side), alternatively at least three sides (or more) (or portions of such sides), among others.

Substrate Selection

In some aspects, the base 30 and/or the cover 60 can comprise any compatible substrate for the practice of the present technology, preferably a biocompatible substrate. The substrate can provide structural integrity or support to the membrane 20 for handling during any of the phases described herein (e.g., manufacture, storage, transport and/or final application). In some instances, the substrate may be a suitable composition that is not chemically or physically altered by cryopreservation solutions (for example, solutions containing Dimethyl Sulfoxide (DMSO). In some aspects, the substrate is also not chemically or physically altered by abrupt or large changes in temperature, and can be used within a wide temperature range (e.g., $-196°$ C. to $60°$ C.$\pm 5°$ C.). In other embodiments, the substrates are made of polymers, copolymers, or biocompatible materials (e.g., plastics) that are thermal compatible and compatible with use with cryopreservation solutions. Suitable plastics include, but are not limited to, low density polyethylene (LDPE), high density polyethylene (HDPE), ECTFE or ETFE copolymer (Ethylene ChloroTriFluoroEthylene or Ethylene tetrafluoroethylene) FEP (fluorinated ethylene propylene), PE (Polyethylene) PP (Polypropylene), PMP (Polymethylpentene), Teflon®, PS (Polystyrene), RESMER™ (also known as RESMER Manufacturing Technology commercially available from Thomas Scientific of Swedesboro, N.J.), EVA, among others. However, it should be appreciated by those skilled in the art that in those embodiments of the present technology in which a cryopreservation media is not utilized, other suitable substrates are envisaged in the practice of the present technology.

In further embodiments of the present technology, the base 30 of the present technology may comprise a material suitable for use with biological or cellular materials, for example, a bio- or cellular-compatible plastic. In additional embodiments, the cover 60 may comprise a material suitable for use with biological or cellular materials, for example, a bio- or cellular-compatible plastic. The plastic may be a composite of different plastics or a homogenous plastic composition. Further such plastics may be combinations of plastics, layers of one or more types of plastics, among other plastics combinations. Again, preferably, the plastics utilized in the practice of the present technology are biocompatible plastics that are further preferably, made of medical grade quality. It is also preferable that the substrates used in the practice of the present technology should be capable of withstanding a wide range of temperature changes ranging from about $40°$ C.$\pm 5°$ C. to about $-196°$ C.$\pm 5°$ C., preferably from about $40°$ C.$\pm 5°$ C. to about $-80°$ C.$\pm 5°$ C. The substrates should be capable of withstanding freezing temperature from about $-80°$ C.$\pm 5°$ C. to about $-196°$ C.$\pm 5°$ C. Substrates should also be capable of remaining at about room temperature (about $20°$ C. to about $25°$ C.$\pm 5°$ C.), during refrigeration (about $4°$ C. to about $8°$ C.$\pm 5°$ C.), and during freezing (from about $-20°$ C.$\pm 5°$ C. to about $-196°$ C.$+/-5°$ C.), alternatively from about $-45°$ C. to about $-50°$ C.$\pm 5°$ C., alternatively from about $-80°$ C. to about $-196°$ C.$\pm 5°$ C. For substrates used with cellular membranes, the substrates should be capable of withstanding a wide range of temperatures from about $60°$ C. to about $-196°$ C. ($+5°$ C.). Suitable biocompatible plastics may include, but are not limited to plastics that withstand exposure to a cryopreservation solution and/or membrane, tissue, graft or other biological material(s) without chemical alteration of its composition and/or alternatively, damaging, injuring, or otherwise harming the membrane (tissue, graft, or other biological material(s)), including harming viable cells associated therewith. Suitable biocompatible plastics can also include, for example, plastics capable for use in 3-D printing applications or manufacturing procedures.

Compositions, Devices, Articles of Manufacture and Systems

Some aspects of the present technology provide compositions, devices, articles of manufacture and systems (e.g., a membrane product package 100) comprising a base 30, a cover 60, and a membrane 20 (tissue, graft or other biological material(s) temporarily associated with each. Again, the base 30 preferably comprises at least one membrane receiving portion 40 wherein the membrane receiving portion temporarily contacts, supports and holds at least one membrane 20 (tissue, graft, or other biological material(s)). The membrane receiving portion 40 also preferably provides sufficient surface traction to maintain the temporary adherence, attachment or connection of the membrane 20 (tissue, graft, or other biological material(s)) to the base 30 without curling of the edges of that membrane (tissue, graft, or other biological material(s)).

In other embodiments, and with reference to FIGS. 5A-7B, the membrane 20 (tissue, graft, or other biological material(s)) is temporarily attached via at least one attachment or connection location associated with the base 30. However, it should be appreciated by those skilled in the art that the membrane 20 (tissue, graft, or other biological material(s)) may be temporarily attached, connected, or adhered to the base by more than one location, preferably two or more, three or more and the like. The locations, as described herein, may be discrete connection or attachment points 22 between the membrane 20 (tissue, graft, or other biological material(s)) and the base 30, including, but not limited to, cauterization points, points attached via a biocompatible adhesive, heat welding, cauterization, ultrasonic welding, and other suitable attachment procedures for use with biological or cellular materials. The number of locations 22 in which the membrane 20 (tissue, graft, or other biological material(s)) is temporarily attached to the base 30 is sufficient to maintain, preferably, the planar orientation of the membrane (tissue, graft, or other biological material(s)) without curling or rolling of the edges thereof on the base, and further to provide a sufficient adhesion, attachment or connection such that the membrane (tissue, graft, or other biological materials(s)) preferably does not significantly move or slide during handling (e.g., when attaching the cover, adding a cryopreservation medium, during storage, during transport, or removing the cover prior to end use application).

The temporary attachment or connection points 22 of the membrane 20 (tissue, graft, or other biological material(s)) to the base 30 may also be in a pattern. For example, a suitable pattern for temporarily attaching or connecting the membrane (tissue, graft, or other biological material(s)) to the base can be at least one connection or attachment point 22 in each corner of the base 30 (or membrane receiving portion 40 thereof); at least one attachment point 22 in a middle portion of the upper edge (e.g., the edge farthest away from the handling portion, if applicable) of the base 30 (or membrane receiving portion 40 thereof), as viewed from the top, looking down at the base 30; and at least one connection or attachment point 22 in a middle portion of the lower edge of the base 30 (or the lower edge of the membrane receiving portion 40 thereof), as viewed from the top, looking down at the base 30. Other suitable patterns are also envisaged, including the exemplary patterns displayed in Tables 7 and 8. Further, additional suitable patterns can also include at least one attachment point in each corner of the membrane receiving portion 40 of the base and at least one attachment point in a middle portion of the lower edge of the base. In some instances the at least one attachment point comprises attachment points at the four corners of the membrane receiving portion; in some instances, the attachment points are additionally in middle portions of the edges defined between the corners of the membrane receiving portion. In an exemplary embodiment, the membrane can be attached to the base at least at the four corners and at least at one point in a middle portion of the upper and/or lower edge. The cover may be attached to the membrane and/or the base by at least one attachment point, preferably at least two attachment points, more preferably at least at three attachment points. The at least one attachment point may be a discrete point in a middle portion along one or more edges of the membrane receiving portion and/or the cover. For example, the three attachment points may be at two middle points along side edges of the membrane receiving portion and/or the cover and at one middle point along the upper edge of the membrane receiving portion.

The Membrane

As provided herein, it should be appreciated that the present technology can be utilized for membranes, tissues, grafts, and other biological materials, collectively referred to herein as "membranes" 20. Thus, the term "membrane" or "membranes" shall be used expansively throughout the instant specification to encompass various cellular and/or biological materials suitable for use in the practice of the present technology. It should also be appreciated by those skilled in the art that "membrane" or "membranes" of the present technology can comprise natural "membranes", synthetic "membranes" or combinations or derivatives thereof. For example, natural membranes can include but are not limited to grafts, naturally derived membranes, and bioengineered membranes comprising living cells, further including, but not limited to, placental membranes, skin grafts, in vitro cultured grafts, tendon grafts, among others. Natural membrane may include allografts, autografts or xenografts. Natural membranes may be derived from mammals, including, for example humans. Bioengineered membranes can include living cells, extracellular matrix, biomolecules, at least one type of cytokine, and combinations or derivatives thereof. Based on the structure of the bioengineered membranes, other suitable materials or biomolecules may be associated with the membrane. Other natural membrane may include, for example, at least one natural fiber, for example, silks. Further non-natural or synthetic membranes, for example, can include but are not limited to membranes containing at least one synthetic fiber or compound, such as nylon, copolymers, polymers, including, but not limited to, PVA (polyvinyl acetate), PLA, (polyactic acid), PGA (polyglycolic acid), PCL (polycaprolactone), PLGA (poly (lactic-co-glycolic) acid), and the like. Further, it should be appreciated that suitable membranes can also include chorionic membrane products, amniotic membrane products, combinations thereof and other placental membrane products. Placental membranes products that can be used with the present technology are disclosed in U.S. application Ser. No. 13/030,507 (Publication No. 2011/0212158); Ser. No. 14/069,894 (Publication No. 2014/0140966); Ser. No. 14/070,035 (Publication No. 2014/0127317); Ser. No. 14/172,940 (Publication No. 2014/0294777); Ser. No. 14/056,101 (filed Oct. 17, 2013); Ser. No. 14/070,040 (Publication No. 2014/0127177); Ser. No. 14/272,343 (Publication No. 2015/0010609); and Ser. No. 14/291,256 (Publication No. 2014/0301986), in the name of Osiris Therapeutics, Inc. of Baltimore, Md., all of which are incorporated by reference in their entireties. Suitable amniotic membrane product includes Grafix® Prime® (Osiris Therapeutics, Columbia, Md.). Suitable chorionic membrane products include, for example, Grafix® Core® (Osiris Therapeutics, Columbia, Md.).

Other suitable grafts for use in the practice of the present technology can also include, for example, grafts containing viable cells. Some suitable grafts, for example contain fibroblasts, epithelial cells, stem cells, mesenchymal stem cells, and compositions comprising various combinations thereof. In some embodiments, the compositions comprising viable fibroblast and epithelial cells.

Suitable bioengineered grafts include grafts in which viable cells, for example fibroblasts, stem cells, epithelial cells, mesenchymal stem cells, which are seeded onto a synthetic or natural membrane. The cells are cultured to provide a sufficient membrane structure. Based on the structure of the bioengineered membranes, other suitable materials or biomolecules may be associated with the membrane. For example, bioengineered grafts may contain extracellular matrix, biomolecules including, but not limited to, cytokines, growth factors, co-stimulatory molecules, proteoglycans, and the like. In some instances, the bioengineered grafts may not include viable cells, and may include other biological membrane components, including, but not limited to, extracellular matrix (e.g., collagen, proteoglycans), biomolecules and the like.

As can be illustrated by the present technology it was surprisingly found that, the described compositions, devices, articles of manufacture and/or systems (e.g., the disclosed support assembly and membrane product package 100) maintain the viability of the temporarily attached, connected, or adhered cells in the membranes. Such an outcome is advantageous as the present technology provides various packaging or packaging system embodiments that support, protect, contain and maintain live cells (e.g., naturally derived membranes or bioengineered membranes) for use in a variety of therapeutic, diagnostic, experimental and/or analytical applications/uses unlike the conventional packaging, packaging systems and non-living cellular packaging products of the prior art.

Further, the compositions, devices, and systems of the present technology also were surprisingly found to maintain the viability, reduce or prevent injury or damage and maintain an ease of removal and application of the cells in the temporarily attached membranes even during a variety of environmental stresses such as manufacturing, processing, cryopreservation, freezing, storage, thawing, transporting, and final application/use of such membranes (or cells). Such outcomes are advantageous for the support, stability and protection of cellular or biological products in a packaging or packaging system not envisaged by the conventional art.

Further, the compositions, devices, articles of manufacture and systems of the present technology may also maintain the integrity of the membrane during a variety of environmental stresses, such as, manufacturing, processing, cryopreservation, freezing, storage, thawing, transporting, and final application/use of such membranes (or cells).

The membrane 20 is preferably placed on the base 30 in an operative position, which maintains the directionality of the membrane (e.g., epithelial cells or tissues on the cover and connective tissue cells or tissue on the base). As described, the base and/or the cover may be labeled to maintain the directionality with a marker or label. Maintaining directionality is important in cellular repair, especially when membranes which mimic the composition of the skin are used. For example, some membranes may have a first side (e.g., lower surface 28) and a second side (e.g., upper surface 26), where the first and second sides have different compositions. For example, amniotic membranes derived from placental tissue have a first side (e.g., lower surface 28) containing stromal cells and a second side (e.g., upper surface 26) containing epithelial cells. For application as a wound or tissue defect repair composition, it is important to maintain the directionality of the membrane. The first side containing stromal cells should make direct contact with the tissue defect or wound, and the epithelial layer should face exterior to the wound, mimicking the structure of the epidermis.

Membranes utilized in the practice of the present technology may be any suitable size and customizable depending on the type of membrane and the particular end application or usage of that membrane. Suitable sizes (length× width) of membrane include, but are not limited to, about 1.5 cm× about 1.5 cm, about 2 cm× about 2 cm, about 3 cm× about 3 cm, about 4 cm× about 4 cm, about 5 cm× about 5 cm, about 6 cm× about 6 cm, about 7 cm× about 7 cm, about 8 cm× about 8 cm, about 7.5 cm× about 15 cm, about 1.5 cm× about 2 cm, about 1.5 cm× about 3 cm, about 2 cm× about 3 cm, about 3 cm× about 4 cm, about 2 cm× about 5 cm, about 3 cm× about 5 cm, about 4 cm× about 5 cm, about 5 cm× about 7 cm, about 5 cm× about 10 cm, about 5 cm× about 15 cm, and include any variations or sizes and ranges there between, in increment of 0.1 cm to 1 cm.

The compositions (e.g., kits) may further comprise a container. The container may be used to store the membrane-containing device or composition (e.g., the membrane product package 100). Additionally, the container may be used for cryopreservation, for handling and shipping of the membrane. The container allows for the addition of cryopreservation solution to the membrane. The container may be a bag or receptacle, or other suitable container. The container is made from a material which is able to be sterilized, can withstand cryopreservation solution and also a wide range of temperatures and/or freeze/thaw cycles without becoming brittle or loosing integrity. Suitable containers include plastic cryopreservation bags, including, for example OSRSFP-90 Cryogenic Storage bag.

In some embodiments, the composition (e.g., kit) further comprises cryopreservation solution. The cryopreservation solution is added to the container containing the membrane-mounted device or composition. Preferably, a sufficient amount of cryopreservation solution is added to the container to protect the membrane during the subsequent freezing steps. The base containing the membrane receiving portion allows for sufficient infusion of the membrane with the cryopreservation solution to maintain viability of the cells contained within the membrane. Suitable cryopreservation solutions are known in the art. In one embodiment, the cryopreservation comprises storage in a cryopreservation medium comprising one or more cell-permeating cryopreservatives, one or more non-cell permeating cryopreservatives, or a combination thereof. Suitable cryopreservatives include, but are not limited to, DMSO, a glycerol, a glycol, a propylene glycol, an ethylene glycol, propanediol, polyethylene glycol (PEG), 1,2-propanediol (PROH) or a combination thereof. In some embodiments, the cryopreservation solution may contain one or more non-cell permeating cryopreservative selected from polyvinyl pyrrolidione, a hydroxyethyl starch, a polysaccharide, a monosaccharide, an alginate, trehalose, raffinose, dextran, human serum albumin, ficoll, lipoproteins, polyvinyl pyrrolidone, hydroxyethyl starch, autologous plasma or a combination thereof. Other examples of useful cryopreservatives are described in Cryopreservation (BioFiles, Volume 5, Number 4 Sigma-Aldrich® Datasheet).

For example, a suitable cryopreservation solution comprises a cryopreservative, in an amount of at least about 0.001% to 100%, suitably in an amount from about 2% to about 20%, preferably about 5% to about 10% by volume. In some instances, the cryopreservation solution comprises at least about 2% cryopreservative. Further, the cryopreservation solution may comprise serum albumin or other suitable proteins. In some embodiments, the cryopreservation solution comprises from about 1% to about 20% serum albumin or other suitable proteins, alternatively from about 1% to about 10%. Serum albumin or other suitable proteins are present to help stabilize the membrane during the freeze-thaw process and to reduce the damage to cells, maintaining viability. Serum albumin may be human serum albumin or bovine serum albumin. The cryopreservation solution may further comprise a physiological buffer or saline, for example, phosphate buffer saline.

The container is filled with sufficient amount of the cryopreservation solution to cover both sides of the membrane. The amount of the cryopreservation solution necessary will depend on the type of container used and the size of the container relative to the size of the membrane-containing composition or device (e.g., membrane product package 100). The lower the amount of cryopreservation solution necessary to cover the composition/device, the faster the composition is able to thaw. Thus, it is desirable to use the least amount of cryopreservation solution that allows for top coverage of the membrane without compromising viability of the cells during the freeze thaw. Further, the smaller the membrane and the smaller the container used, the less cryopreservation solution can be used.

In some embodiments, a bag is used containing cryopreservation solution in an amount from about 7 ml to about 50 ml, alternatively from about 10 ml to about 50 ml, alternatively from about 15 ml to about 50 ml, alternatively from about 15 ml to about 25 ml. In one preferred embodiment, about 15 ml of cryopreservation solution is added to the container or bag. The amount of cryopreservation solution can be sufficient to fully submerge the membrane. The amount will depend on the size of the bag used and the size of the membrane being cryopreserved. If a small bag is being used with a small (e.g. smaller than 2 cm×2 cm membrane), about 3 ml to about 10 ml, alternatively 3 ml to about 7 ml of cryopreservation solution may be used.

In some embodiments a container is used containing from about 7 ml to about 50 ml, alternatively from about 5 ml to about 20 ml, alternatively from about 7 ml to about 20 ml, alternatively from about 7 ml to about 15 ml. The amount of cryopreservation solution can be sufficient to fully submerge the membrane within the container. The amount will depend on the size of the container used and the size of the membrane being cryopreserved.

In some embodiments, the amount of cryopreservation solution is sufficient to protect cells during the freezing and subsequent thawing procedures. In some embodiments, at least 70% cell viability is maintained after a freeze-thaw. In some aspects, at least 75% cell viability is maintained, alternatively about 80% cell viability is maintained, alternatively 85% cell viability is maintained, alternatively about 90% cell viability is maintained, alternatively about 95% cell viability is maintained. In some embodiments, at viability of the membrane is at least 70%, at least 71%, at least 72%, at least 73%, at least 74%, at least 75%, at least 75%, at least 78%, at least 80%, at least 82%, at least 85%, at least 88%, at least 89%, at least 90%, at least 92%, and percentages in between.

In some embodiments, the amount of cryopreservation solution is sufficient to protect the structural, architectural, and or 3-D structure of the membrane, including a cellular matrixes. In some embodiments, the cryopreservation solution contains a cryopreservative in an amount of 0.01% to about 100%, alternatively from about 2% to about 100%. In some embodiments, the cryopreservation solution contains polysaccharides or monosaccharides.

Methods of Using, Employing, or Applying the Compositions, Devices, Articles of Manufacture, or Systems In various embodiments of the present technology, a method of making a cryopreserved packaging product, cryopreserved cellular packaging product, or cryopreserved therapeutic packaged product (e.g., a membrane product package 100) is provided, among others. The methods comprise, for example, the steps of providing at least one membrane to be cryopreserved; adhering, connecting or attaching, preferably temporarily, the membrane to at least one membrane receiving portion of a base; adhering at least one cover to the membrane and base; placing the then membrane-containing base and cover into a storage receptacle; filling the storage receptacle with a sufficient amount of at least one cryopreservation media (e.g., a cryopreservation solution) to submerge, immerse, or permeate (partially or completely) the membrane containing base and cover combination; placing the storage receptacle within a refrigerated environment at about 2° C. to about 8° C. for at least about 10 minutes, preferably about 30 to about 60 minutes; and then subsequently subjecting the membrane containing base and cover combination to a freezing environment, thus freezing the container to preferably about −80° C. The cryopreserved product (i.e., the membrane containing base and cover combination of the present technology) should remain frozen until thawed for use. In other embodiments, the method of adhering, connecting or attaching the membrane to the base comprises cauterizing the membrane to the base at least at one point, alternatively at least at three points, alternatively at least at five points, alternatively at least at six points. Further, the method of adhering the membrane to the base could comprise using a biocompatible adhesive to adhere at least one point between the membrane and the base, preferably at least five points, alternatively at least six points. In other embodiments, the cover is adhered, connected or attached to the membrane-containing base by cauterizing at least at one point, alternatively at least at three points. Further, the adhering can be done by using an adhesive at least at one point between the cover and the membrane-containing base, at least at two points, at least at three points.

In some methodology embodiments of the present technology, a method of cryopreserving a membrane is provided comprising the steps of: a) preparing a membrane; b) adhering the membrane to the device (or composition, article of manufacture, or system of the present technology) as described herein; c) placing the device comprising the membrane in a sterile receptacle; d) applying a cryopreservation media (e.g., a cryopreservation solution) to the device in the receptacle, wherein the device comprising the membrane is partially or completely submersed, immersed, or is permeated in the cryopreservation media, and e) cryopreserving the sterile holder and device (i.e., containing the selected membrane) at a temperature of about −80° C. In other embodiments, the method of cryopreserving a membrane may comprise the steps of: preparing a composition (or device, article of manufacture, or system of the present technology) as described herein; placing the composition in a sterile receptacle; applying a cryopreservation media (again, e.g., a cryopreservation solution) to the device in the receptacle, wherein the device (i.e., further comprising the membrane) is submerged, immersed, permeated partially or fully in the cryopreservation media; and cryopreserving the sterile receptacle and device at a temperature of about −80° C.±5° C. to about −196° C.±5° C.

Kits

Packaging kits comprising the compositions, devices, articles of manufacture, devices and systems of the present technology are also provided. The kits can comprise, for example, a device comprising a base containing a membrane receiving portion and a cover with or without the temporarily attached membrane as described herein. The kits can further comprise a device (composition, article of manufacture, or system) of the present technology and instructions for adhering, attaching or connecting, preferably temporarily, the membrane as described herein to, preferably between, the base and the cover in some manner or fashion that meets the goals and advantageous of the present technology as described herein. In other aspects, the kits can provide further instructions on maintaining the directionality of the membrane when applied, attached, adhered or connected to the cover and/or base as well when stored, transported, handled and finally applied to a wound or tissue defect, or when used in another application. For example, such instructions can provide placing a first side of the membrane facing the base and a second side facing the cover. Thus, the directionality of the membrane can be maintained, for example, during storage and application. The kit may further comprise at least one adhesive, such as at least one bio-adhesive. Thus, in some aspects, the kits of the present technology provide instructions for preferably temporarily adhering, attaching, or connecting the membrane to the base at least at one point, alternatively adhering, connecting, or attaching (preferably temporarily) the membrane at least at three points to the base, alternatively adhering, connecting or attaching (preferably temporarily) the membrane at least at five points to the base, alternatively adhering, attaching or connecting (preferably temporarily) the membrane at least at six points to the base. In other respective aspects, the instructions of the present technology can provide instructions as to how to cauterize the membrane at varying points to the base. In other aspects, the instructions of the present technology can provide a method of using a bio-adhesive to adhere, attach, or connect (again, preferably temporarily) the membrane to the base at specific points by applying the bio-sealer to at least one point between the membrane and base. In some aspects, the kit comprises instructions on adhering, connecting or attaching the cover to the base, wherein the membrane is located between the cover and the base. In some embodiments, the cover is adhered, connected or attached to the membrane at least at one point, preferably at least at three points. In such embodiments, the adherence may be to the membrane itself or pass through the membrane to the base. The points of attachment may be discrete points along the edge, over the partial or whole length of one or edges, or over the entire surface area.

Kits of the present technology for treating a tissue defect are also provided herein. The kits may comprise a composition (or device, or article of manufacture, or system) comprising at least one membrane, a base and at least one cover as described herein. The kit may also provide for a cryopreserved membrane as described herein. The kit can also comprise at least one set of instructions for thawing the membrane. The kit may further comprise instructions, for example, for rinsing or washing the membrane (e.g., once thawed if previously cryopreserved) and instructions for applying (e.g., in an oriented manner or position) the membrane to at least one wound or at least one tissue defect of a patient (human or animal). Such kits of the present technology may also include at least one preparation guide for preparing a tissue suitable for use in accordance with the practice of the present technology. Such kits may include, for example, an application guide as to how to apply the membrane to a wound or tissue defect. Alternatively, the application guide may comprise, for example, instructions on how to remove the cover from the membrane-bound base and methods of how to slide the membrane from the base onto a suitable treatment site or for other use. Further, such kits may contain a sizing chart and instructions for sizing the membrane to a preferable size depending on the application or treatment site size. Such an outcome of the present technology allows for a health care provider to customize or tailor the membrane selected prior to or during the resultant procedure with the patient. Such real time or on-demand capability has been surprisingly found by use of the present technology and overcome several limitations of the prior art in which fixed membrane products and product sizes do not allow for such customization, much less on a real time or on-demand basis.

In still further embodiments, the kits of the present technology further comprise a cutting device, for example scissors or a scalpel. In other embodiments, the kit may contain a buffer or thawing medium as well as other media necessary for the particular use or application of the membrane contained therein. In other embodiments, the kits of the present technology may contain, for example, forceps, tweezers, and other handling media. In some embodiments, the kit further comprises a container.

Methods Concerning the Compositions, Devices, Articles of Manufacture and Systems of the Present Invention The methods, compositions, devices, articles of manufacture and systems of the present technology described herein provide for a "membrane" as set forth herein which maintains or provides at least about 70% viable cells for application to an end user (e.g., to a wound or a tissue defect) or for other diagnostic, experimental, or analytical uses. It has been surprisingly found that the methods, compositions, devices, articles of manufacture and systems of the present technology allow for the support and protection of living or fresh cellular materials for later use post-manufacture, storage, preservation, transport and handling prior to final application or use unlike that of the prior art. Moreover, significant therapeutic advantages can be achieved by the methods, compositions, articles of manufacture, devices and systems of the present technology due to the significantly enhanced and maintained cellular viability. Further, costs are reduced, and treatment modalities are streamlined or enhanced, all while providing a convenient and ease to use approach for a handler of the presently described packaging and/or packaging products.

Methods of applying a membrane to a patient (human or animal) in need thereof are provided with respect to the present technology. At least one method comprises the steps of (i) obtaining a device, composition of matter, article of manufacture, or system of the present technology described herein containing a membrane or biological composition described herein which has been cryopreserved and stored at about −80° C. to about −196° C. The method can further comprise the steps of (ii) thawing the membrane; (iii) optionally, rinsing or washing the membrane with a sterile physiological solution or other suitable biological medium; (iv) removing the cover from the membrane and base; (v) and applying the membrane from the base onto the patient as a unitary outcome or step. Optionally, the method can also comprise the steps of (i) assessing the orientation of the membrane as to the cover and the base to retain the orientation (or directionality) of the membrane prior to application; and (ii) applying the membrane with the proper orientation as provided by the composition, device, articles of manufacture, or system of the present technology. It should be appreciated by those skilled in the art and as further described herein that the orientation can be provided in a variety of manners including an optional directional marker or label separate from or inclusive of the cover, the base, or both the cover and the base.

In other embodiments, a method of applying a membrane to a patient (human or animal) in need thereof comprises the steps of: 1) thawing a receptacle (e.g., a bag, or other suitable receptacle for biological or cellular materials) containing the cryopreserved product of the present technology to about room temperature; 2) removing the cryopreserved product from the receptacle; 3) rinsing or washing the cryopreserved product in a physiological buffer, physiological medium, or other suitable biological or cellular medium; 4) removing the cover from the base and membrane; and 5) sliding the membrane from the base in a singular step and applying the membrane onto the area to be treated on the patient. The step of sliding the membrane from the base may include the further steps of breaking the temporary adherence, connection or attachment between the membrane and the base at the at least one connection or attachment location.

It has been surprisingly found that the compositions, devices, articles of manufacture, systems and methods of the present technology provide for the membrane to be slid from the base in a manner which allows the handler (e.g., a health care provider) to maintain the directionality of the membrane when applied to the affected area or location without causing the membrane to curl, fold over onto itself, or otherwise be significantly injured or damaged during the application process. Such an ability, provides for additional therapeutic outcomes of the present technology in that a greater portion of the treatment area receives the membrane; a greater amount of the viable cellular material of the membrane is applied to the treatment area; potentially fewer applications of the membrane need to be utilized to the patient (thus leading to potentially improved treatment times); increased patient compliance; increased health care provider receptivity to the use of such cellular products, reduced cost, and other advantageous outcomes. Further, because more of the end product of the present technology can be preserved and applied, less waste occurs than conventional products of a potential similar nature.

Moreover, because the end products of the present technology are supplied in such a manner as described herein, the end user has the ability to tailor the size and shape of the end product such that the resultant membrane to be applied to a particular affected area (or other application) can be done in a customized manner and potentially in a real time, on demand manner as needed. This is significantly different and improved over other conventional products of a similar nature currently available.

Finally, the end products and method of application of the present technology also surprisingly allow and provide for increased handling comfort and increased safety within the medical discipline because the end product edges can be smoothed. In doing so, the end product of the present technology is easier to handle and does not puncture or cut the handlers appendages. This is significant in the health care industry where blood borne disease transmission is to be prevented.

Further, the present technology surprisingly allows for a reduced thaw time. As demonstrated in the examples herein, the thaw time for cryopreserved membranes in the devices, compositions, articles of manufacture or systems of the present technology is 10 fold reduced as compared to conventionally packaged membranes. This reduction in thaw time not only limits the time that the membrane is exposed to cryopreservative factors, but also provides much for convenience for the end user/health care provider that is applying the membrane to a subject. As demonstrated, that thaw time for packaged membrane of the present technology is about 3 to 4 minutes, as opposed to at least 30 minutes for a conventionally packaged membrane. Also, in some instances, the reduction of time exposed to thawed cryopreservation solution also can lead to increased viability of the cells contained within the membrane.

It should also be appreciated by those skilled in the art that the "membranes" of the presently described technology utilized in the further methods of the present technology can be used for application to a number of different types of wounds or tissue defects. Tissue defects can include, but not limited to, wounds, abrasions, lacerations, incisions, ulcers, corneal wounds, among others. Ulcers include, but are not limited to, dermal ulcers. Optionally, the wound is a laceration, scrape, thermal or chemical burn, puncture, or wound caused by a projectile. Optionally, the wound is an epidermal wound, skin wound, chronic wound, acute wound, external wound, internal wounds, or congenital wound. Such wounds may be accidental or deliberate, e.g., wounds caused during or as an adjunct to a surgical procedure. Optionally, the wound may be closed surgically prior to administration.

The membranes disclosed herein are also useful in treating a number of wounds including: tendon repair, cartilage repair (e.g. femoral condyle, tibial plateau), ACL (anterior crucial ligament) replacement at the tunnel/bone interface, dental tissue augmentation, fistulas (e.g., Crohn's disease, jejunal-tube-based, tracheoesophageal), missing tissue at adhesion barriers (e.g. nasal septum repair, vaginal wall repair, abdominal wall repair, tumor resection), dermal wounds (e.g. partial thickness burns, toxic epidermal necrolysis, epidermolysis bullosa, pyoderma gangrenosum, ulcers e.g. diabetic ulcers (e.g. foot), venous leg ulcers), surgical wounds, hernia repair, tendon repair, bladder repair, periosteum replacement, keloids, organ lacerations, epithelial defects, and repair or replacement of a tympanic membrane.

For the variety of methods of application of the membrane via the present technology, it is preferable that the application be via topical administration. Alternatively, it can be used during surgical applications.

In another embodiment, a membrane is administered to a subject to topically treat a burn. Optionally, the burn is a first-degree burn, second-degree burn (partial thickness burns), third degree burn (full thickness burns), infection of burn wound, infection of excised and unexcised burn wound, loss of epithelium from a previously grafted or healed burn, or burn wound impetigo.

In a still further embodiment, a membrane is topically administered by placing the membrane directly over the skin of the subject, e.g., on the stratum corneum, on the site of the wound, so that the wound is covered, for example, using an adhesive tape.

It should be appreciated by those skilled in the art that other forms of administering or applying the present technology are also envisaged. For example, the membrane delivered by the device, composition, article of manufacture or system of the present technology may be administered as an implant, e.g., as a subcutaneous implant.

In yet further embodiment, a membrane is topically, cutaneously, subcutaneously, and the like administered to the epidermis to reduce features of aging skin or scarring. Such treatment is also usefully combined with so-called cosmetic surgery (e.g. rhinoplasty, rhytidectomy, etc.).

In another embodiment, a membrane is topically administered to the epidermis to accelerate healing associated with a dermal ablation procedure or a dermal abrasion procedure (e.g. including laser ablation, thermal ablation, electric ablation, deep dermal ablation, sub-dermal ablation, fractional ablation, and microdermal abrasion).

Other pathologies that may be treated with present technology include, for example, traumatic wounds (e.g. civilian and military wounds), surgical scars and wounds, spinal fusions, spinal cord injury, avascular necrosis, reconstructive surgeries, ablations, and ischemia.

A membrane prepared and applied according to the present technology can optionally be used to reduce adhesion or fibrosis of a wound. Postoperative fibrosis is a natural consequence of all surgically-based wound healing. By example, postoperative peridural adhesion results in tethering, traction, and compression of the thecal sac and nerve roots, which cause a recurrence of hyperesthesia that typically manifests a few months after laminectomy surgery. Repeated surgery for removal of scar tissue is associated with poor outcome and increased risk of injury because of the difficulty of identifying neural structures that are surrounded by scar tissue. Therefore, experimental and clinical studies have primarily focused on preventing the adhesion of scar tissue to the dura matter and nerve roots. Spinal adhesions have been implicated as a major contributing factor in failure of spine surgery. Fibrotic scar tissue can cause compression and tethering of nerve roots, which can be associated with recurrent pain and physical impairment.

In additional aspects and embodiments of the present technology, methods of maintaining the directionality of a membrane during processing, storage, cryopreservation, or during application to a subject (human or animal) are disclosed. The methods may comprise, for example, the steps of preparing a membrane, wherein the membrane has a first a second side, wherein the first and second side comprise different compositions; and adhering the membrane to the device (composition, article of manufacture or system also of the present technology) disclosed herein, where the membrane is disposed partially or completely between the base and cover. The method can also comprise the step of adhering, attaching or connecting the membrane to the cover and the base wherein the first side of the membrane is facing and connects or attaches to the base and the second side of the membrane is facing and connects or attaches to the cover. Such a method may further comprise the step of labeling the base and/or cover by a marker (e.g., a symbol) to indicate the orientation or directionality of application of the product, or alternatively the directionality of the membrane to be applied or utilized in a manner where orientation is desired. In some instances, the base is marked for orientation and the membrane is attached via a predetermined orientation to the base.

In other embodiments, the methods of the present technology further comprise the step of determining the adherence or surface traction of the first side and the second side of the membrane to, for example, the cover and/or the base, and orientating the membrane such that the side of the membrane with higher surface traction is facing the base. In some embodiments, the membrane comprises a first side comprising stromal cells and a second side comprising endothelial cells, wherein the first side is orientated to face the base. In other embodiments, the first side of the membrane has a greater adherence to the cover.

In the preceding paragraphs, use of the singular may include the plural except where specifically indicated. As used herein, the words "a," "an," and "the" mean "one or more," unless otherwise specified. In addition, where aspects of the present technology are described with reference to lists of alternatives, the technology includes any individual member or subgroup of the list of alternatives and any combinations of one or more thereof. Moreover, the disclosures of all patents and publications, including published patent applications, are hereby incorporated by reference in their entireties to the same extent as if each patent and publication were specifically and individually incorporated by reference.

It is to be understood that the scope of the present technology is not to be limited to the specific embodiments described above. The present technology may be practiced other than as particularly described and still be within the scope of the accompanying claims. Likewise, the following examples are presented in order to more fully illustrate the present technology. They should in no way be construed, however, as limiting the broad scope of the technology disclosed herein.

The presently described technology and its advantages will be better understood by reference to the following examples. These examples are provided to describe non-exhaustive embodiments of the present technology. By providing these examples, the scope of the presently described and claimed technology is not limited in spirit or scope. It will be understood by those skilled in the art that the full scope of the presently described technology encompasses at least the subject matter defined by the claims appending this specification, and any alterations, modifications, derivatives, combinations, or equivalents of those claims. Further, the citations provided herein are hereby incorporated by reference for the cited subject matter.

EXAMPLES

Example 1: Producing a Composition, Device, Article of Manufacture, or System According to the Present Technology The following example demonstrates the use of a base and a cover of the present technology with a membrane, e.g. a placental product. The following procedure was used:

1. Placental membranes were prepared for placement in the packaging or handling compositions, devices, articles of manufacture or systems of the present technology. Methods of preparing placental products, for example, are disclosed in U.S. patent application Ser. No. 13/030,507 (Publication No. 2011/0212158); Ser. No. 14/069,894 (Publication No. 2014/0140966); Ser. No. 14/070,035 (Publication No. 2014/0127317); Ser. No. 14/172,940 (Publication No. 2014/0294777); Ser. No. 14/056,101 (filed Oct. 17, 2013); Ser. No. 14/070,040 (Publication No. 2014/0127177); Ser. No. 14/272,343 (Publication No. 2015/0010609); and Ser. No. 14/291,256 (Publication No. 2014/0301986), which are incorporated herein by reference in their entireties.

2. In a pre-processing step, the membrane is prepared to size by any suitable means. In this instance, the membrane was placed on temporary nitrocellulose paper substrate to allow for convenient handling and provides a template for cutting to size.

3. Tissue was removed from the nitrocellulose paper using forceps and transferred onto the perforated plastic base. For amniotic membrane, the stromal side is placed facing the perforations. The tissue was adjusted to cover the entire area of the membrane receiving portion of the plastic base. Any extra tissue was folded over the base.

4. The tissue was cauterized at the points indicated in FIGS. 7A-7B. FIGS. 7A-7B depict a schematic representation of cautery points on the plastic pieces (6 points on the base, left; 3 points on the cover, right). Side portions of a cautery pen were used to cauterize the four corners and the middle point of the cover. A tip portion of a cautery pen was used to cauterize the base middle point.

5. The cover was placed on top of the tissue and base, aligning the corner edges.

6. The cover was cauterized to the membrane and base using the side portions of the cautery pen at the three points shown in FIG. 7B.

Example 2: Cell Viability and Epithelial Growth Factor (EGF) Content of Membranes Samples were prepared as described in Example 1. After at least 48 hours of deep freezing in a −80° C. freezer, batches of 8 samples were taken out and thawed in a room temperature water bath 18-24° C. and tested to ensure minimum cell viability (>70%) and for the amniotic membrane, EGF contents (>7.8 pg/ml). Results are shown in Tables 11-13 described herein.

Tissue samples of appropriate size (5×5 cm or 2×2 cm) were used for validation assays. Refer to Table 1 for the number of membranes to be tested per lot and the tests performed (Eastman Tritan MP100 Copolyester (Tritan™).

TABLE 1

Amniotic and Chorionic Membrane Testing Scheme

| Test | Method | Amniotic Membrane | | Chorionic Membrane | |
| --- | --- | --- | --- | --- | --- |
| | | Nitrocellulose | Tritan ™ | Nitrocellulose | Tritan ™ |
| Cell Viability | Cell count | 1-5 cm × 5 cm | 1-5 cm × 5 cm | 1-5 cm × 5 cm | 1-5 cm × 5 cm |
| EGF concentration | ELISA | 2-2 cm × 2 cm | 2-2 cm × 2 cm | N/A | N/A |

Cell counts were performed. Briefly, amniotic membrane was digested with collagenase and chorionic membrane was digested with collagenase and trypsin for 15-45 min at 37° C. with constant agitation. Once tissue was completely digested or it reached the longest time point, the cell suspension is either passed through a cell strainer and wash strainer with Dulbecco's Modified Eagle Medium (DMEM) (chorionic membrane) or centrifuged and the cell/tissue pellet resuspended in trypsin and incubated at 37° C. for another 5-15 min. After incubation the cell suspension is passed through a cell strainer and wash strainer with DMEM (amniotic membrane). Centrifuge for another 10 min to obtain cell pellets. DMEM was added and cell counting performed using a hemocytometer with Trypan blue exclusion under a light microscope. Digested amniotic or chorionic samples were diluted to the appropriate ratio in Trypan Blue and the number of cells in 5x 0.0001 ml squares were counted.

Human EGF ELISA assay was performed to measure the contents of human EGF of amniotic membrane. Briefly, two 2×2 cm tissues were used. Membrane was snap frozen in liquid nitrogen for 5 minutes. 500 μl of calibrator diluents was added and the tissue was homogenized in a Tissue Lyser chamber for 3 minutes at 50 Hz. Samples were centrifuged at 14,000 rpm for 10 minutes at 4° C. The supernatant was used for ELISA assay. The assay is described in details in manufacturer manual. Three lots of human amniotic membrane were randomly selected and assayed.

Example 3: Evaluation Methods of Different Base Configurations

Mounted membranes were inspected for attachment with the packaging. The passing criteria included that 1) all components of the mounting applicator (the support assembly) and tissue stay together; and 2) at least 75% of the tissue should stay flat on the mounting applicator for all the following procedures:

Rinsing in Dulbecco's Modified Eagle Medium (DPBS)

Forceps were used to hold a corner of the base without touching the mounted membrane. The membrane was rinsed in saline solution. The membrane was monitored for detachment from the base.

Filling of the Cryoprotectant Solution

The membrane assembled within the base and cover (as in Example 1) was placed into an OSRSFP-90 Cryogenic Storage bag. The bag was filled with 50 ml cryoprotectant solution. The membrane was monitored for detachment from the plastic base, and the cover was monitored for detachment from the membrane and/or plastic base.

Rinsing Post-Thawed

After at least 18 hours of deep freezing at −80° C., amniotic membrane was thawed in sufficient volume of room temperature saline (such that the liquid surface could cover the entire Cryogenic Storage bag) until all ice crystals disappeared. The membrane was monitored for detachment from the plastic base during thawing. Once thawed, the membrane was removed from the OSRSFP-90 Cryogenic Storage bag and placed in the rinse basin containing sterile saline. The membrane was monitored during rinsing for detachment from the base and the cover was monitored for detachment from the membrane and/or plastic base.

Application

The cover was removed and the tissue was observed to determine if more than 75% of the tissue stayed attached to the base. The membrane was promptly applied onto the wound such that its orientation was maintained throughout the process.

Example 4: Non-Nitrocellulose Approaches

Coated nitrocellulose was found to introduce chemicals of animal origins into subjects, thereby rendering the coated nitrocellulose unsuitable for some patients. Non-nitrocellulose approaches were therefore evaluated.

For the prototypes developed under this category, plastics were identified as a material that provided for easy application in that membranes and tissues can slide off the plastic onto the wound bed while maintaining their orientation. This configuration included two plastic pieces generally identified as a "cover" and a "base". The base was used to maintain the orientation of the tissue, includes a portion having a non-uniform surface (a tissue/membrane receiving portion), and provides a platform for the sliding application. The cover provides protection for the tissue/membrane during manufacturing, transport, storage, and use (e.g., thawing). The cover can minimize the fluid shear stress acting on the epithelial layer of the tissue (membrane) during the filling of the cryopreservation solution as well as during the transit and handling of the cryogenic storage bags to/from a refrigerator into a deep freezer. Different chemical and mechanical fixation/attachment methods have been evaluated for the base and are summarized in Table 2 (below). The perforation sandwich plastic design was selected for further development as it passed all evaluation criteria listed in Example 3

TABLE 2

Description of non-nitrocellulose paper prototypes and their evaluation results.

| Prototype name | Prototype description |
| --- | --- |
| Poly-D-Lysin-treated plastic | Coat plastic with 1 mg/ml Poly-D-Lysin solution for 3 hrs at 37° C. Place amnion onto the coated plastic with stromal side facing plastic. Incubate at 37° C. for 3 hrs |

TABLE 2-continued

Description of non-nitrocellulose paper prototypes and their evaluation results.

| Prototype name | Prototype description |
| --- | --- |
| Sandpaper-treated Plastic | Plastic were treated with sandpaper. The entire surface feels rough to touch. |
| Microplate Devices UniSeal ™ | Sandwich the tissue in between the two parts of a Microplate Uniseal, which contain an adhesive-backed clear polyetyrene seal film and a water-resistant paper. |
| 4 pins | Fix four corners of tissue samples with pins so it stretches out to a square shape |
| 4 straight slit corners | Cut four corners of the base piece into slits, then insert each corner of the tissue inside the slits |
| 4 straight slit corners with hard paper inserts | Cut four corners of the base into slits; align tissue onto a piece of thick paper (blue) that was cut to the size of the units, i.e. 5 × 5 (cm$^2$) or 2 × 2 (cm$^2$); then tuck the paper with the tissue inside the slits |
| Two straight slits on the base with cover piece sealed together with base | Cut two angled slits on the base sheet to anchor the tissue. Cut two corners parallel to the first two slits on the plastic cover. Seal two plastic sheets together shown as the grey line. Place the tissue on the base sheet and tuck two base corners inside the two slits |
| 4 clipping round corners | Create four corners of the base piece to half-moon shape using a 3 mm biopsy punch; then tuck tissue in; tighten the tissue by pressing the back side of the opening until hearing a click sound |
| Frame with plastic lamination | Make a paper frame the same size as the units, i.e. 5 × 5 (cm$^2$) or 2 × 2 (cm$^2$); lay it on the top of one piece of plastic; then insert tissue samples inside the frame; put another piece of same size plastic to enclose everything; laminate the four sides |
| Clamp | The tissue membrane is fastened in between two parts of the clamp and fastened by the screw |
| Plastic "Sandwich" with perforations | Holes (5 mm in diameter) were punched using a comb hole puncher paper binder binding machine |

Plastic Selection

Based on general performance of the above described embodiments, the plastic "sandwich" configuration was selected for further evaluation. The next step was to identify plastic that: is compatible with living tissue, low temperature, and DMSO; and complies with USP class VI testing (for plastics)

Copolyesters and polycarbonates were considered as potential materials for development. Tritan™ is described in the examples below as it was provided in a convenient validation package.

Example 5: Testing of Perforated Sandwich Design on Tritan™ Sheets Perforation Parameters Sizes of the perforations and center-to-center spacing between adjacent perforations were varied (Table 3). Four combinations of perforation size and center-to-center spacing were chosen as listed in Table 3. Placental membranes, either amniotic or chorionic membrane, were mounted on perforated plastic and evaluated according to performance criteria described in Example 3 including: Rinsing in DPBS; Filling of the Cryoprotectant solution; Rinsing post-thawed; and Application.

TABLE 3

Perforation parameters testing scheme

| Perforation Diameter | Center-to-Center Spacing |
| --- | --- |
| 4 mm | 10 mm |
| 2 mm | 10 mm |
| 2 mm | 5 mm |
| 1 mm | 4 mm |

Neiko Hand Held Power Punch kit or a 1 mm biopsy punch was used to manually create the perforations. AutoCAD file was generated and an evenly distributed perforation design was printed onto the Tritan™ sheet for easy tracing. 2 mm and 4 mm were selected because perforation configuration with 5 mm holes was not able to pass the visual inspection criteria listed. The schematic representations of the perforation design and results are summarized in FIG. 10.

The results show placental tissue mounted on Tritan™ sheet with 1 mm perforation spaced 4 mm apart meet all criteria listed. Therefore these perforation size and spacing parameters were selected for further cell viability and EGF testing.

Example 6: Evaluation of Different Perforation Patterns on the Tritan™ Sheet

Because the high number of holes potentially leads to higher manufacturing cost, we sought to test whether different perforation pattern design would allow us to reduce the number of holes needed to provide strong bonding (maintain shape and attachment).

1 mm diameter was used and different perforation patterns were tested as described in FIG. 11. AutoCAD files of the pattern were generated and printed onto Tritan™ sheets. Holes were created using 1 mm biopsy punches according to the printed design. Amniotic membrane was then mounted onto the plastic. Top solid plastic pieces were used to cover amniotic membrane mounted on the perforated plastic. The evaluation of each pattern was done based on the criteria listed above. The evaluation of each pattern was done based on the criteria described in Example 3, including: Rinsing in DPBS; Filling of the Cryoprotectant solution; Rinsing post-thawed; and Application.

Results are summarized in FIG. 11. None of the described designs provided results that were as effective as the most effective patterns in FIG. 10.

Results are summarized in Table 5. None of the described designs provided results that were as effective as the most effective patterns in Table 4.

Example 7: Evaluation of Perforations on the Front or Back or Both Pieces of the Plastic Different combinations of the perforated and solid plastic pieces were tested. In our hands the combination of the solid plastic cover and the perforated plastic base allows the good attachment of amniotic membrane with easy removal of the cover without lifting/detaching amniotic membrane from the base. Results are summarized in Table 6.

TABLE 6

Comparison between different perforation positions

| Configuration | Comments |
| --- | --- |
| Perforation on the cover only | amniotic membrane tends to adhere to the cover |
| Perforations on both cover and base | Could not consistently keep more than 75% membrane on the base |
| Perforations on the base only | The cover was easy to be removed amniotic membrane attaches well to the plastic base |

Example 8: Different Cautery Systems and Cautery Patterns

The improved two-piece packaging system embodiments are suitably held together with the tissue to provide as one unit to the customers. Here we investigated different cautery systems and cautery patterns as the fixing method so that the chosen cautery system and pattern 1) can effectively fix the tissues as well as the two plastic pieces together without breaking apart; 2) avoid burned brown spots of the tissue; and 3) is cost-effective and can be used in a cleanroom environment.

Cautery Systems

Different cautery systems were evaluated as seen in Table 6. The maximum number of cautery points for each system was recorded. The performance criteria were described in Example 3. The Bovine Fine Tip Cautery (704° C.) configuration and the Bovine Vasectomy Micro Fine Tip Cautery configuration were found to provide the best performance and be the most economical. The other configurations were found to have higher costs, provide fewer cautery points, produce more burned products, or have a tendency to catch fire.

TABLE 6

Comparison Between Different Cautery Systems

| Configuration | Number of Cauterizations |
| --- | --- |
| Gemini Cautery Kit | N/A |
| Bovie Micro Fine Tip Cautery, 454° C. | 31~54 |
| Accu-temp ½" shaft with fine tip, 677° C. | 27 |
| Bovie Fine Tip Cautery, 704° C. | 99~168 |
| Bovie Vasectomy Micro Fine Tip Cautery, 871° C. | 90 |
| Bovie Vasectomy Micro Fine Tip Cautery, 982° C. | N/A |
| Accu-Temp Vasector Fine Tip Cautery, 982° C. | N/A |
| Bovie Micro Fine Tip Cautery, 1093° C. | 464 |
| Bovie Fine Tip Cautery, 816-1149° C. | N/A |
| Bovie Fine Tip Cautery, 1204° C. | N/A |

Cautery Patterns

Different cautery patterns were evaluated for amniotic membrane as seen in FIG. 12 and chorionic membrane as seen in FIG. 13. The goal for these embodiments was to use the least number of cautery points to meet all performance criteria.

Design 1 (with eight points) was found to work best for amniotic membrane, with five points on the base and three points on the cover. For chorionic, Design 1 was found to work the best, with six points on the base and three points on the cover. In order to simplify the manufacturing process, it is contemplated that Design 1 for the chorionic membrane can be used to support both placental membranes.

For the amniotic membrane experiment, Designs 2-9 either did not consistently meet the performance criteria or were found to have too many cautery points (resulting in an overly complicated manufacturing process). Similarly, for the chorionic membrane experiment, Designs 2-9 either did not consistently meet the performance criteria or were found to have too many cautery points (resulting in an overly complicated manufacturing process). However, it is contemplated that Designs 2-9 for the amniotic membrane experiment and Designs 2-9 for the chorionic membrane experiment can be used as disclosed herein to support a membrane or other biological product.

Example 9: Effect of New Plastic Packaging on Placental Products

Results in Table 9-11 demonstrated that the plastic packaging has no negative effect on cell viability for both membranes (amniotic and chorionic) and EGF content for amniotic membranes.

Effect of New Plastic Packaging on Cell Viability of Placental Membranes

TABLE 9

Evaluation of cell viability of amniotic membrane on Tritan ™

| Donor Information | Conditions | Cell Viability | Assay Acceptance (>70%) |
| --- | --- | --- | --- |
| 1 | Control | 77% | Pass |
|   | Tritan ™ | 70% | Pass |
| 2 | Control | 79% | Pass |
|   | Tritan ™ | 73% | Pass |
| 3 | Control | 71% | Pass |
|   | Tritan ™ | 78% | Pass |
| 4 | Control | 78% | Pass |
|   | Tritan ™ | 73% | Pass |
| 5 | Control | 94% | Pass |
|   | Tritan ™ | 90% | Pass |
| 6 | Control | 87% | Pass |
|   | Tritan ™ | 84% | Pass |

TABLE 10

Cell Viability of chorionic membrane

| Donor Information | Conditions | Cell Viability | Assay Acceptance (>70%) |
| --- | --- | --- | --- |
| 7 | Control | 81% | Pass |
|   | Tritan ™ | 87% | Pass |
| 8 | Control | 86% | Pass |
|   | Tritan ™ | 79% | Pass |
| 9 | Control | 81% | Pass |
|   | Tritan ™ | 89% | Pass |

Effect of New Plastic Packaging on EGF Content of Amniotic Membrane

TABLE 11

Evaluation of EGF contents of amniotic membrane on Tritan ™ by ELISA

| Donor Information | Conditions | EGF Concentration (pg/ml) | Assay Acceptance (>7.8 pg/ml) |
| --- | --- | --- | --- |
| 10 | Control | 109.5 | Pass |
|  | Tritan ™ | 157.3 | Pass |
| 11 | Control | 33.3 | Pass |
|  | Tritan ™ | 43.5 | Pass |
| 12 | Control | 95.6 | Pass |
|  | Tritan ™ | 69.6 | Pass |

Thus, as exemplified by the above-described illustrative embodiments, a mounting applicator (support assembly) has been designed for membrane and tissues that can be derived from natural or non-natural (i.e., synthetic) sources. The applicator (support assembly) can replace current technology based on nitrocellulose paper and provides a simple application procedure for the end user. As further disclosed herein, the applicator (support assembly) can comprise a cover and a base, suitably of a plastic material, that are positioned to accept a membrane between the cover and base. The base has an irregular surface, such as a perforated portion, which receives a membrane, having a size generally corresponding to its cover, and a tab area for handling purposes. The base can be sealed to the tissue (e.g., membrane to base) at a plurality of points, and additional seal points can secure the cover to the membrane and/or base to make a "sandwich" configuration.

Example 10: Method of Thawing and Application of a Cryopreserved Membrane Product of the Present Technology Placental membrane products can be cryopreserved and stored frozen and shipped to the end user in a Styrofoam container.

Thawing:

Prior to use of the placental membrane product, two basins, a bottle of sterile saline, scissors, sterile forceps and gloves can be gathered. One large basin can be used for thawing and a smaller sterile basin for rinsing.

The placental membrane product can be removed from storage. The placental product can be packaged in a carton box with tamper evident labels on each side of the box which describe product name and size, lot number, unit number, date of expiry, part number and required storage conditions. Inside the box, the product can be provided in a chevron-type peel pouch, along with the package insert and chart labels to be used on the patient's records.

The outer pouch can be peeled open and the inner cryobag can be placed into the large thaw basin. To ensure the orientation of the placental product is correct, the cryobag can be placed in the thaw basin with the label side up so it is visible to read. Sufficient warm water or saline can be added into the large thaw basin containing the placental product to completely cover the cryobag. The water temperature should not exceed about 39° C. or 102° F.

While the product is thawing, sterile saline can be added to the small rinse basin. Once all ice crystals are completely thawed, the placental product (graft) can be removed from the cryobag. The placental product should remain in the thaw basin for no more than 15 minutes. Holding the cryobag with the port side down, the top of the bag can be cut with sterile scissors, taking care not to cut near the graft. With sterile forceps, the placental product (graft) can be removed from the cryobag.

In an operating room setting, sterile tools and basins should be used, and aseptic technique should be applied when thawing the placental product.

Next, the placental product can be placed into the sterile rinse basin and confirm that the lettering on the base is oriented correctly (e.g., the base correctly reads "PRIME" or "CORE" as shown in FIGS. 6A and 7A). This can allow for correct orientation for placement onto a wound, for example, for amniotic membranes. The membrane should be applied to the subject or patient within one hour.

Application:

The index wound identified for placental membrane placement should be appropriately cleaned and debrided.

To apply the placental product, the base can be held on the labeled tab, and the top plastic cover can be removed. Once the cover is off, the placental product can be slid from the plastic backing onto the wound bed using aseptic technique.

Next, using sterile forceps, sterile gloves, or sterile moist cotton applicators, the graft can be maneuvered to ensure that the entire wound bed is covered. The graft should be in direct contact with all surfaces of the wound bed, including the edges.

Excess membrane can be placed on the edges of the wound, can extend over the surrounding healthy tissue, or can be folded into the wound bed. Any air bubbles and pockets that may exist between the graft and the wound should be removed for best results.

The placental product can optionally be covered with a non-adherent dressing, and an appropriate compressive or outer layer dressing can be applied, depending on wound type.

Example 11: Comparison of Thawing Time for Placental Tissue Mounted on Either Disclosed Support Assembly (Tritan™) or Nitrocellulose Paper Objective: To investigate whether there is a significant reduction of thawing time when using the disclosed support assembly (base and cover), the current thawing procedures were performed on placental membrane mounted on the disclosed support assembly and on nitrocellulose paper.

Methods:

Two samples were taken from two lots of placental tissue, with one sample of each lot packaged in the disclosed support assembly and the other sample of each log packaged on nitrocellulose paper. All samples were removed from the deep freezer (−80° C.).

A cryobag containing the placental tissue was positioned in the thawing basin, which was filled with room temperature water.

Record Thawing Time

For placental tissue on nitrocellulose paper, the timer was stopped when all ice crystals were not visible.

For placental tissue on the support assembly disclosed herein, the timer was stopped when the plastic of the support assembly could be separated from its surrounding ice crystals.

TABLE 12

| | Results: | |
|---|---|---|
| | Thawing Time (min) | |
| Donor | Nitrocellulose paper | Tritan ™ |
| A | 24 | 3 |
| B | 28 | 4 |

Because of the unique packaging design (plastic-membrane-plastic "sandwich") of the disclosed support assembly, when thawing is sufficient to loosen surrounding ice crystals, it is safe to take the support assembly out of the bag and simply remove the ice chunks on either side of the plastic without damaging the membrane enclosed in between.

In contrast, for placental tissue mounted on nitrocellulose paper, the thawing had to be complete, i.e. all ice crystals disappear. Otherwise, the weight of the ice could tear the membrane or cause the membrane to fall off of the nitrocellulose paper, leading to self-folding when thawing is complete.

Conclusion: The disclosed plastic packaging allowed a 8-10 times faster thawing time than conventional nitrocellulose paper packaging.

Exemplary Devices, Methods, and Kits

In various exemplary aspects, disclosed herein is a support assembly for supporting a biological product in an operative position, the support assembly comprising: a base having a longitudinal axis and comprising a product receiving portion, the product receiving portion having a top surface and an opposed bottom surface that are spaced apart relative to a vertical axis that is perpendicular to the longitudinal axis of the base, wherein the product receiving portion comprises an traction-creating feature, wherein the traction-creating feature is selected from the group consisting of (i) a rough top surface and (ii) a plurality of perforations extending between the top and bottom surfaces of the product receiving portion; and a cover having a longitudinal axis, a top surface, and an opposed bottom surface, wherein the cover is configured for releasable coupling to the base in a product-covering position, and wherein, in the product-covering position, the cover overlies the product receiving portion of the base, wherein the base and the cover are configured to cooperate to support the biological product in the operative position, wherein, in the operative position, the biological product is positioned in engagement with at least a portion of the top surface of the product receiving portion of the base and at least a portion of the bottom surface of the cover.

In another exemplary aspect, the base further comprises a handling portion positioned adjacent to the product receiving portion relative to the longitudinal axis of the base. In another exemplary aspect, in the product-covering position, the cover does not overlap with the handling portion of the base. In another exemplary aspect, the handling portion comprises a tab. In another exemplary aspect, the handling portion of the base has a longitudinal length and a width, wherein the product receiving portion of the base has a longitudinal length and a width, and wherein the width of the product receiving portion is equal to the width of the handling portion.

In another exemplary aspect, in the product-covering position, the longitudinal axis of the cover is positioned in substantial alignment with the longitudinal axis of the base. In another exemplary aspect, the product receiving portion of the base has a longitudinal length and a width, wherein the cover has a longitudinal length and a width, and wherein the longitudinal length of the cover is substantially equal to the longitudinal length of the product receiving portion. In another exemplary aspect, the width of the cover is substantially equal to the width of the product receiving portion.

In another exemplary aspect, the cover has a plurality of corners, and at least one of the corners of the cover is rounded. In another exemplary aspect, the cover has four rounded corners. In another exemplary aspect, the product receiving portion of the base has two rounded corners, and wherein, in the product-covering position, two rounded corners of the cover overlie the two rounded corners of the product receiving portion of the base.

In another exemplary aspect, the traction-creating feature of the product receiving portion of the base comprises a plurality of perforations. In another exemplary aspect, the plurality of perforations of the product receiving portion of the base are substantially evenly distributed throughout the product receiving portion. In another exemplary aspect, the plurality of perforations of the product receiving portion of the base are randomly distributed throughout the product receiving portion. In another exemplary aspect, each perforation of the plurality of perforations has a respective diameter ranging from about 0.1 mm to about 5 mm. In another exemplary aspect, each perforation of the plurality of perforations has a respective center point, and wherein the center points of neighboring perforations are spaced apart by a distance ranging from about 0.35 mm to about 10 mm.

In another exemplary aspect, the traction-creating feature of the product receiving portion of the base comprises a rough top surface.

In further exemplary aspects, the disclosed support assembly can be provided as part of a membrane product package, which further comprises a membrane positioned in an operative position between the product receiving portion of the base and the cover, wherein the membrane is positioned in engagement with at least a portion of the top surface of the product receiving portion of the base and at least a portion of the bottom surface of the cover.

In another exemplary aspect, the membrane is attached to the top surface of the product receiving portion of the base at least one attachment point. In another exemplary aspect, the membrane is attached to the top surface of the product receiving portion of the base at least three attachment points. In another exemplary aspect, the membrane is attached to the top surface of the product receiving portion of the base at least five attachment points. In another exemplary aspect, the top surface of the product receiving portion of the base is attached to the cover at least one attachment point.

In another exemplary aspect, the cover is attached to the membrane at least one attachment point. In another exemplary aspect, the cover is attached to the membrane at least two attachment points. In another exemplary aspect, the cover is attached to the membrane at least three attachment points. In another exemplary aspect, the top surface of the product receiving portion of the base is attached to the cover at least one attachment point.

In another exemplary aspect, the top surface of the product receiving portion of the base is attached to the cover at least one attachment point. In another exemplary aspect, the top surface of the product receiving portion of the base is attached to the cover at at least three attachment points.

In another exemplary aspect, the attachment points between the base and the membrane, between the cover and the membrane, and/or between the base and the cover are cauterization points.

In another exemplary aspect, the membrane is a natural membrane.

In another exemplary aspect, the membrane is a placental tissue product. In another exemplary aspect, the membrane is a chorionic membrane product. In another exemplary aspect, the membrane is an amniotic membrane product.

In another exemplary aspect, the membrane is a synthetic membrane.

In another exemplary aspect, the membrane and the top surface of the product receiving portion of the base have sufficient surface traction to maintain the membrane in the operative position following removal of the cover from the base.

In another exemplary aspect, the membrane and the top surface of the product receiving portion of the base have a first surface traction, wherein the membrane and the cover have a second surface traction, and wherein the second surface traction is lower than the first surface traction.

In additional exemplary aspects, the disclosed support assembly can be used in a method of producing a membrane product package, the method comprising positioning a membrane in an operative position between the product receiving portion of the base and the cover of the support assembly, wherein the membrane is positioned in engagement with at least a portion of the top surface of the product receiving portion of the base and at least a portion of the bottom surface of the cover.

In another exemplary aspect, the step of positioning the membrane in the operative position comprises: attaching the membrane to the top surface of the product receiving portion at a plurality of attachment points; and attaching the membrane to the cover at a plurality of attachments points. In another exemplary aspect, when the traction-creating feature of the product receiving portion comprises a plurality of perforations, the method further comprises positioning the base, the membrane, and the cover within a cryopreservation solution, wherein the plurality of perforations of the product receiving portion provide contact between the membrane and the cryopreservation solution sufficient to cryopreserve the membrane.

In further exemplary aspects, a method of applying a membrane is provided, comprising removing the cover from the disclosed membrane product package to expose a top surface of the membrane; disengaging the membrane from the top surface of the product receiving portion of the base; and selectively applying the membrane to a desired location on a human or animal patient.

In still further exemplary aspects, the disclosed membrane product package can be provided as part of a kit for repairing a tissue defect. In another exemplary aspect, the kit can further comprise a container that encloses the membrane product package, wherein the container can be selectively opened to provide access to the membrane product package. In another exemplary aspect, the kit can further comprise instructions for applying the membrane of the membrane product package to repair the tissue defect. In still further exemplary aspects, the kit can further comprise a cryopreservation solution. In still further exemplary aspects, the kit can further comprise a basin configured to receive the membrane product package. In still further exemplary aspects, the kit can further comprise scissors. In still further exemplary aspects, the kit can further comprise tweezers.

More generally, in further exemplary aspects, disclosed herein is a device (e.g., a support assembly) comprising: a base comprising a product (e.g., membrane) receiving portion; and a cover; and at least one location in which the base and the cover are in communication (at least one temporary or removable attachment between the back and the cover.

In another exemplary aspect, the membrane receiving portion comprises a traction-creating feature (e.g., a structured surface). In another exemplary aspect, the traction-creating feature (e.g., structured surface) is selected from the group consisting of an abraded surface, a rough surface, a scratched surface, a surface comprising a plurality of perforations; a surface comprising a plurality of channels; a surface comprising a plurality of grooves; a surface comprising a plurality of indentations.

In another exemplary aspect, the traction-creating feature (e.g., structured surface) of the membrane receiving portion comprises a surface comprising a plurality of perforations. In another exemplary aspect, the plurality of perforations are uniformly distributed throughout the membrane receiving portion. In another exemplary aspect, the plurality of perforations are randomly distributed throughout the membrane receiving portion. In another exemplary aspects, the plurality of perforations are evenly distributed in close relationship to each other throughout the membrane receiving portion to provide sufficient surface traction for the membrane to adhere to the base. In another exemplary aspect, the plurality of perforations are about 1 mm to about 5 mm in diameter and each perforation is from 4 mm to about 10 mm apart as measured center to center. In another exemplary aspect, the plurality of perforations are from about 0.1 mm to about 5 mm in diameter. In another exemplary aspect, the plurality of perforations are from about 0.1 mm to about 1 mm in diameter. In another exemplary aspect, the perforations are spaced about 0.35 mm to about 10 mm apart as measured center to center. In another exemplary aspect, the perforations are spaced about 4 mm to about 10 mm apart as measured center to center. In another aspect, the plurality of perforations are of a geometrical shape or a nongeometrical shape. In another exemplary aspect, the plurality of perforations are a shape selected from the group consisting of oval, rectangular, square, diamond, trapezoid, star, hexagonal, octagonal, semi-circular, crescent, or a combination thereof.

In another exemplary aspect, the traction-creating feature of the membrane receiving portion comprises a rough plastic surface.

In another exemplary aspect, the base comprises at least one plastic or polymer.

In another exemplary aspect, the cover comprises at least one plastic or polymer.

In another exemplary aspect, the plastic base further comprises a handling portion adjacent to the membrane receiving portion.

In another exemplary aspect, the handling portion does not overlap with the cover.

In another exemplary aspect, the handling portion comprises a tab. In another exemplary aspect, the tab spans the entire width of the base.

In another exemplary aspect, the cover spans the entire membrane receiving portion of the base.

In another exemplary aspect, the at least one location in which the base and cover are in communication comprises at least one cauterization point, at least one point made by an ultrasonic welder, or at least one point comprising an adhesive. In another exemplary aspect, the at least one location in which the base and cover are in communication comprises a plurality of points.

In another exemplary aspect, the base and the plastic cover are formed from a single piece of plastic.

In another exemplary aspect, the base and the plastic cover are separate pieces of plastic.

In another exemplary aspect, the base and the cover are made of the same plastic.

In another exemplary aspect, base comprises plastic selected from the group consisting of polycarbonate, copolyester, low density polyethylene (LDPE), high density polyethylene (HDPE), ECTFE copolymer, ETFE copolymer, FEP (fluorinated ethylene propylene), PE (Polyethylene), PP (Polypropylene), PMP (Polymethylpentene), Teflon, PS (Polystyrene), EVA, and Tritan copolyester MP100.

In another exemplary aspect, the plastic of the cover is selected from the group consisting of polycarbonate, copolyester, low density polyethylene (LDPE), high density polyethylene (HDPE), ECTFE copolymer, ETFE copolymer, FEP (fluorinated ethylene propylene), PE (Polyethylene), PP (Polypropylene), PMP (Polymethylpentene), Teflon, PS (Polystyrene), EVA, and Tritan copolyester MP100.

In another exemplary aspect, the cover is a solid sheet of plastic.

In another exemplary aspect, the cover has non-sharp corners. In another exemplary aspect, the corners are rounded.

In another exemplary aspect, the base has non-sharp corners. In another exemplary aspect, the base has rounded edges.

In another exemplary aspect, the cover has four rounded corners.

In another exemplary aspect, the device reduces damage to a membrane during cryopreservation. In another exemplary aspect, the device is sufficient to reduce damage to a membrane due to fluid shear force during addition or submersion into cryopreservation solution.

In another exemplary aspect, the device provides sufficient permeation of the cryopreservation solution to a membrane.

In another exemplary aspect, the device retains its integrity when immersed in a cryopreservation solution.

In another exemplary aspect, the device retains its integrity during a freeze-thaw cycle. In another exemplary aspect, the freeze thaw cycle includes a freezing step of about −45° C. to −196° C. for a cellular membrane and about −18° C. to about −196° C. for an acellular membrane.

In another exemplary aspect, the cover is the same size as the membrane receiving portion of the base.

In another exemplary aspect, the base and cover are free of impurities. In another exemplary aspect, the base and cover are free of particulates or oils or other chemicals that may interfere with the viability or therapeutic efficacy of the membrane.

In another exemplary aspect, the at least one location in which the base and the cover are in communication comprises a plurality of points. In another exemplary aspect, the plurality of points comprise a plurality of cauterization points, wherein the plurality of cauterization points comprises at least two cauterization points, preferably at least three cauterization points.

In another exemplary aspect, the at least one location in which the base and cover are in communication allows for the retention of the cover to the base through a cryopreservation step, a freezing step and a thawing step.

In another exemplary aspect, a membrane is between the base and the cover. In another exemplary aspect, the membrane is attached to the base by at least three points. In another exemplary aspect, the membrane is attached to the base by at least five points. In another exemplary aspect, the membrane is attached to the base by at least six points. In another exemplary aspect, the cover is in communication with the base at least at two points. In another exemplary aspect, the cover is in communication with the base at least at three points. In another exemplary aspect, the membrane is a selected from the group consisting of a natural membrane, a synthetic membrane or a combination thereof. In another exemplary aspect, the membrane is a natural membrane. In another exemplary aspect, the membrane is a placental tissue product. In another exemplary aspect, the membrane is a synthetic membrane. In another exemplary aspect, the membrane is a combination of natural and synthetic membrane. In another exemplary aspect, the membrane is bioengineered. In another exemplary aspect, the membrane is a chorionic membrane product. In another exemplary aspect, the membrane is an amniotic membrane product. In another exemplary aspect, the membrane is an in vitro derived tissue. In another exemplary aspect, the membrane is a cultured tissue equivalent.

In another exemplary aspect, the device withstands freezing at about −80° C. to about −196° C. without losing integrity.

In another exemplary aspect, the device is resistant to chemical or physical alteration by cryopreservation solutions. In another exemplary aspect, the cryopreservation solution comprises DMSO.

In another exemplary aspect, the membrane receiving portion is about 1.5 cm×1.5 cm, about 2 cm×3 cm, about 3 cm×4 cm, or about 5 cm×5 cm.

In another exemplary aspect, the device allows for sufficient contact between the membrane and the cryopreservation solution to sufficiently cryopreserve the natural membrane to maintain viability. In another exemplary aspect, the viability is at least 70% after at least one freeze-thaw cycle in cryopreservation solution. In another exemplary aspect, the membrane maintains sufficient viability. In another exemplary aspect, the membrane has at least 70% viability.

In another exemplary aspect, the base and the membrane have sufficient surface traction to maintain the membrane on the base.

In another exemplary aspect, the surface traction between the membrane and the cover is lower than the surface traction between the membrane and the base.

In another exemplary aspect, the plurality of perforations, plurality of grooves, or plurality of channels is sufficient to cryopreserve the membrane by providing contact between the membrane and the cryopreservation solution.

In another exemplary aspect, the membrane receiving portion of the base is about 1.5 cm×1.5 cm, about 1.5 cm×2.0 cm, about 2 cm×2 cm, about 2 cm×3 cm, about 3 cm×4 cm, about 5 cm×5 cm, about 5 cm×7 cm, or about 7.5 cm×15 cm.

In another exemplary aspect, the handling portion comprises a label to indicate orientation. In another exemplary aspect, the label to indicate orientation is a word. In another exemplary aspect, the label to indicate orientation is a symbol.

In further exemplary aspects, the disclosed device can be used in a method of maintaining the directionality of a membrane during storage, cryopreservation, or during application to a subject, the method comprising: a) preparing a tissue, wherein the tissue is orientated having a first and a second side, wherein the first and second side comprise different composition; b) adhering the membrane to the disclosed device, wherein the membrane is disposed between the base and the cover, wherein the first side of the membrane is facing the base and the second side of the membrane is facing the cover, and wherein the device further comprises a label to indicate orientation. In another exemplary aspect, the membrane is a placental tissue. In another exemplary aspect, the first side of the membrane comprises stromal cells and the second side comprises epithelial cells. In another exemplary aspect, the first side of the membrane has greater adherence to the base than the second side of the membrane. In another exemplary aspect, the base provides a handling portion that comprises the label to indicate orientation. In another exemplary aspect, the label is a word. In another exemplary aspect, the label is a symbol.

In still further exemplary aspects, the disclosed device can be used in a method of maintaining integrity of a membrane during cryopreservation, the method comprising: providing the disclosed device; adhering a membrane to at least an area of the membrane receiving portion of the base; adhering the cover to the base, wherein the membrane is between the cover and the base; and placing the device comprising the membrane into a container; and contacting the container with sterile cryopreservation solution, wherein the device comprising the membrane is submerged in the cryopreservation solution; and cryopreserving the container at a temperature of about −80° C. to about −196° C. for an membrane containing cells and about −18° C. to about −196° C. for an acellular membrane, wherein the integrity of the membrane is maintained once the membrane is thawed to room temperature.

In additional exemplary aspects, the disclosed device can be provided as part of a kit, which further comprises instructions for adhering a membrane between the base and the cover of the device, wherein the base and the cover have at least one location which is adapted to be in communication with each other. In another exemplary aspect, the kit further comprises an adhesive that is biologically compatible. In another exemplary aspect, the instructions further comprise a method of adhering the base to a first side of the membrane, wherein the method comprises applying the adhesive to at least one location between the base and the membrane to form a membrane-covered base. In another The kit of claim 156, wherein the instructions provide a method of adhering the cover to base wherein the membrane is located between said cover and base, wherein the method comprises applying the adhesive to at least one point between the cover and the membrane-covered base. In another exemplary aspect, the instructions further comprise a step of cauterizing at least one point of the cover to the base, wherein the membrane is located between the cover and base. In another exemplary aspect, the instructions further comprise a method of maintaining the directionality of the membrane, the method comprising the steps of adhering a first side of the membrane to the base. In another exemplary aspect, the kit further comprises instructions for cryopreserving the device comprising a membrane. In another exemplary aspect, the step of cryopreserving comprises freezing the device containing the membrane at −80° C. In another exemplary aspect, the kit further comprises instructions for thawing the cryopreserved device. In another exemplary aspect, the kit further comprises instructions of applying the membrane to a patient (human or animal) in need thereof.

Exemplary Compositions, Methods, and Kits

In further exemplary aspects, disclosed is a composition comprising: (a) a base comprising a membrane receiving portion; (b) a membrane; (c) a cover; and (d) at least one location in which the base and the cover are in communication, wherein the membrane is positioned between the base and the cover.

In another exemplary aspect, the base further comprises a handling portion. In another exemplary aspect, the handling portion is adjacent to the membrane receiving portion. In another exemplary aspect, the handling portion comprises a tab.

In another exemplary aspect, the membrane receiving portion comprises a plurality of perforations. In another exemplary aspect, the plurality of perforations are uniformly distributed throughout the membrane receiving portion. In another exemplary aspect, the plurality of perforations are randomly distributed throughout the membrane receiving portion. In another exemplary aspect, the plurality of perforations are evenly distributed in close relationship to each other throughout the membrane receiving portion to provide sufficient surface traction for the membrane to adhere to the base. In another exemplary aspect, the plurality of perforations are about 1 mm to about 5 mm in diameter and the each perforation is from 4 mm to about 10 mm apart as measured center to center. In another exemplary aspect, the plurality of perforations are from about 0.1 mm to about 5 mm diameter. In another exemplary aspect, the plurality of perforations are from about 0.1 mm to about 1 mm diameter. In another exemplary aspect, the perforations are spaced about 0.35 mm to about 10 mm apart as measured center to center. In another exemplary aspect, the perforations are spaced about 4 mm to about 10 mm apart as measured center to center. In another exemplary aspect, the plurality of perforations are of any geometrical shape or non-geometrical shape. In another exemplary aspect, the plurality of perforations are a shape selected from the group consisting of oval, rectangular, square, diamond, trapezoid, star, hexagonal, octagonal, semi-circular, crescent, or a combination thereof. In another exemplary aspect, the plurality of perforations are sufficient to cryopreserve the membrane by providing contact between the membrane and the cryopreservation solution.

In another exemplary aspect, the base and the cover comprise a single sheet of plastic. In another exemplary aspect, the single sheet of plastic is folded to form a base and a cover.

In another exemplary aspect, the membrane receiving portion is selected from the group consisting of an abraded surface, a rough surface, a scratched surface, a surface comprising a plurality of perforations; a surface comprising a plurality of channels; a surface comprising a plurality of grooves; or a surface comprising a plurality of indentations.

In another exemplary aspect, the base comprises at least one plastic.

In another exemplary aspect, the cover comprises at least one plastic.

In another exemplary aspect, the handling portion does not overlap with the cover. In another exemplary aspect, the handling portion spans the entire width of the base. In another exemplary aspect, the cover spans the entire membrane receiving portion of the base.

In another exemplary aspect, the base and the plastic cover are separate pieces of plastic.

In another exemplary aspect, the plastic of the base is selected from the group consisting of polycarbonate, copolyester, low density polyethylene (LDPE), high density polyethylene (HDPE), ECTFE copolymer, ETFE copolymer, FEP (fluorinated ethylene propylene), PE (Polyethylene), PP (Polypropylene), PMP (Polymethylpentene), Teflon, PS (Polystyrene), EVA, and Tritan copolyester MP100.

In another exemplary aspect, the plastic of the cover is selected from the group consisting of polycarbonate, copolyester, low density polyethylene (LDPE), high density polyethylene (HDPE), ECTFE copolymer, ETFE copolymer, FEP (fluorinated ethylene propylene), PE (Polyethylene), PP (Polypropylene), PMP (Polymethylpentene), Teflon, PS (Polystyrene), EVA, and Tritan copolyester MP100.

In another exemplary aspect, the cover is a solid sheet of plastic.

In another exemplary aspect, a first side of the cover is in contact with a second side of the membrane and the first side of the membrane is in contact with a first side of the base, and wherein the first side of the cover has a lower surface tension than a first side of the base.

In another exemplary aspect, the cover has no sharp corners or edges. In another exemplary aspect, the corners are rounded.

In another exemplary aspect, the base has no sharp corners or edges. In another exemplary aspect, the base has rounded corners.

In another exemplary aspect, the composition is sufficient to reduce damage to the membrane during cryopreservation. In another exemplary aspect, the composition is sufficient to reduce damage to the membrane due to fluid shear force during addition or submersion into cryopreservation solution.

In another exemplary aspect, the composition retains its integrity in a cryopreservation solution.

In another exemplary aspect, the composition retains its integrity during a freeze-thaw cycle. In another exemplary aspect, the freeze thaw cycle includes a freezing step of $-40°$ C. to $-196°$ C. for a cellular membrane and $-18°$ C. to $-196°$ C. for an acellular membrane.

In another exemplary aspect, the cover is the same size as the membrane receiving portion of the base.

In another exemplary aspect, the base and cover are free from impurities.

In another exemplary aspect, the base and the cover are free of particulates or oils or other chemicals that may interfere with the viability or therapeutic efficacy of the membrane.

In another exemplary aspect, the at least one location in which the base and the cover are in communication comprises a plurality of points. In another exemplary aspect, the plurality of points comprise a plurality of cauterization points.

In another exemplary aspect, the at least one location in which the base and cover are in communication allows for the retention of the cover to the base through a cryopreservation step, a freezing step and a thawing step.

In another exemplary aspect, the membrane is attached to the base by at least three points. In another exemplary aspect, the membrane is attached to the base by at least five points. In another exemplary aspect, the membrane is attached to the base by at least six points.

In another exemplary aspect, the cover is in communication with the base and membrane at least at two points. In another exemplary aspect, the cover is in communication with the base at least at three points.

In another exemplary aspect, the membrane is a selected from the group consisting of a natural membrane, a synthetic membrane or a combination thereof.

In another exemplary aspect, the membrane is a natural membrane.

In another exemplary aspect, the membrane is a placental tissue product. In another exemplary aspect, the membrane is a chorionic membrane product. In another exemplary aspect, the membrane is an amniotic membrane product.

In another exemplary aspect, the membrane is a synthetic membrane.

In another exemplary aspect, the membrane is a combination of natural and synthetic membrane.

In another exemplary aspect, the membrane is bioengineered membrane.

In another exemplary aspect, the membrane is an in vitro derived tissue.

In another exemplary aspect, the membrane is a cultured tissue equivalent.

In another exemplary aspect, the membrane is a graft.

In another exemplary aspect, the composition withstands freezing at $-80°$ C. without losing integrity.

In another exemplary aspect, the composition is resistant to chemical alteration by a cryopreservation solution. In another exemplary aspect, the cryopreservation solution comprises DMSO.

In another exemplary aspect, the membrane receiving portion is 2 cm×2 cm. In another exemplary aspect, the membrane receiving portion of the base is about 1.5 cm×1.5 cm, about 1.5 cm×2 cm, about 2 cm×2 cm, about 2 cm×3 cm, about 3 cm×4 cm, about 5 cm×5 cm, about 5 cm×7 cm, or about 7.5 cm×15 cm.

In another exemplary aspect, the composition allows for sufficient contact between the membrane and the cryopreservation solution to sufficiently cryopreserve the natural membrane to maintain viability.

In another exemplary aspect, the viability of the membrane is at least 70% after at least one freeze-thaw cycle in cryopreservation solution.

In another exemplary aspect, the base and the membrane have sufficient surface traction to maintain the membrane on the base when submerged in a solution.

In another exemplary aspect, the surface traction between a second side of the membrane and the cover is lower than the surface traction between a first side of the membrane and the base.

In another exemplary aspect, the membrane maintains sufficient viability after cryopreservation. In another exemplary aspect, the viability of the membrane is at least 70%.

In another exemplary aspect, the membrane is a graft.

In another exemplary aspect, the base or the cover is labeled to indicate orientation. In another exemplary aspect, the label is located on the base. In another exemplary aspect, the label is located on a handling portion of the base. In another exemplary aspect, the label is located on the cover. In another exemplary aspect, the label is located on a handling portion adjacent to the cover.

In further exemplary aspects, the disclosed composition can be used in a method of applying a membrane to a patient (human or animal) in need thereof, the method comprising: obtaining the disclosed composition, wherein the composition has been cryopreserved and frozen; thawing the composition; rinsing the membrane in a sterile physiological solution; removing the cover from the membrane and base; and applying the membrane from the base onto the patient (human or animal) to retain directionality of the membrane.

In still further exemplary aspects, the disclosed composition can be used in a method of treating a wound, the method comprising applying a membrane of the composition to a patient in need thereof.

In additional exemplary aspects, the disclosed composition can be provided as a cryopreserved membrane composition, which further comprises a cryopreservation solution. In another exemplary aspect, the cryopreservation solution comprises DMSO. In another exemplary aspect, the cryopreservation solution comprises about 5% DMSO. In another exemplary aspect, the cryopreservation solution comprises about 2% to about 10% DMSO. In another exemplary aspect, the cryopreservation solution further comprises about 1% to about 20% serum albumin. In another exemplary aspect, the cryopreserved membrane composition further comprises physiological saline.

In further exemplary aspects, the disclosed cryopreserved membrane composition can be provided as part of a kit, which further comprises instructions for applying the cryopreserved membrane to a tissue defect. In another exemplary aspect, the kit further comprises instructions for thawing the cryopreserved composition. In another exemplary aspect, the kit comprises further instructions on maintaining the directionality of the membrane while being applied to the tissue defect. In another exemplary aspect, the tissue defect is a wound. In another exemplary aspect, the kit further comprises instructions for removal of the cover. In another exemplary aspect, the kit further comprises instructions for maintaining the directionality of the membrane. In another exemplary aspect, the kit further comprises instructions for removing the membrane from the base.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, certain changes and modifications may be practiced within the scope of the appended claims.

What is claimed is:

1. A membrane product package comprising:
   a base having a longitudinal axis and comprising a product receiving portion, the product receiving portion having a top surface and an opposed bottom surface that are spaced apart relative to a vertical axis that is perpendicular to the longitudinal axis of the base, wherein the product receiving portion comprises a traction-creating feature, wherein the traction-creating feature comprises one or more of the following: (i) a rough top surface, (ii) a plurality of perforations extending between the top and bottom surfaces of the product receiving portion, (iii) a surface comprising a plurality of channels, (iv) a surface comprising a plurality of grooves, (v) a surface comprising a plurality of indentations, or (vi) a surface comprising a plurality of porations; and
   a cover having a longitudinal axis, a top surface, and an opposed bottom surface, wherein the cover is configured for releasable coupling to the base in a product-covering position, and wherein, in the product-covering position, the cover overlies the product receiving portion of the base; and
   a membrane positioned in an operative position between the product receiving portion of the base and the cover, wherein the membrane is a placental tissue product, a tissue graft, an in vitro cultured graft, a tendon graft, or a bioengineered membrane comprising living cells, wherein the membrane is positioned in engagement with at least a portion of the top surface of the product receiving portion of the base and at least a portion of the bottom surface of the cover, wherein the base and the cover cooperate to support the membrane in the operative position.

2. The membrane product package of claim 1, wherein the base further comprises a handling portion position adjacent to the product receiving portion relative to the longitudinal axis of the base.

3. The membrane product package of claim 2, wherein, in the product-covering position, the cover does not overlap with the handling portion of the base.

4. The membrane product package of claim 1, wherein in the product-covering position, the longitudinal axis of the cover is positioned in a substantial alignment with the longitudinal axis of the base.

5. The membrane product package of claim 4, wherein the product receiving portion of the base has a longitudinal length and a width, wherein the cover has a longitudinal length and a width, and wherein the longitudinal length of the cover 1s substantially equal to the longitudinal length of the product receiving portion.

6. The membrane product package of claim 5, wherein the width of the cover is substantially equal to the width of the product receiving portion.

7. The membrane product package of claim 1, wherein the cover has a plurality of corners, and wherein at least one of the corners of the cover is rounded.

8. The membrane product package of claim 7, wherein the cover has four rounded corners.

9. The membrane product package of claim 8, wherein the product receiving portion of the base has two rounded corners, and wherein, in the product-covering position, two rounded corners of the cover overlie the two rounded corners of the product receiving portion of the base.

10. The membrane product package of claim 1, wherein the traction-creating feature of the product receiving portion comprises a plurality of perforations.

11. The membrane product package of claim 10, wherein the plurality of perforations of the product receiving portion of the base are substantially evenly distributed throughout the product receiving portion.

12. The membrane product package of claim 10, wherein the plurality of perforations of the product receiving portion of the base are randomly distributed throughout the product receiving portion.

13. The membrane product package of claim 10, wherein each perforation of the plurality of perforations has a respective diameter ranging from about 0.1 mm to about 5 mm.

14. The membrane product package of claim 10, wherein each perforation of the plurality of perforations has a respective center point, and wherein the center points of neighboring perforations are spaced apart by a distance ranging from about 0.35 mm to about 10 mm.

15. The membrane product package of claim 1, wherein the membrane is attached to the top surface of the product receiving portion of the base at least one attachment point.

16. The membrane product package of claim 15, wherein the membrane is attached to the top surface of the product receiving portion of the base at least three attachment points.

17. The membrane product package of claim 15, wherein the top surface of the product receiving portion of the base is attached to the cover at least one attachment point.

18. The membrane product package of claim 15, wherein the cover is attached to the membrane at least one attachment point.

19. The membrane product package of claim 18, wherein the cover is attached to the membrane at least two attachment points.

20. The membrane product package of claim 18, wherein the top surface of the product receiving portion of the base is attached to the cover at least one attachment point.

21. The membrane product package of claim 1, wherein the top surface of the product receiving portion of the base is attached to the cover at least one attachment point.

22. The membrane product package of claim 1, wherein the membrane is a chorionic membrane product.

23. The membrane product package of claim 1, wherein the membrane is an amniotic membrane product.

24. The membrane product package of claim 1, wherein the membrane and the top surface of the product receiving portion of the base have sufficient surface traction to maintain the membrane in the operative position following removal of the cover from the base.

25. The membrane product package of claim 1, wherein the membrane and the top surface of the product receiving portion of the base have a first surface traction, wherein the membrane and the cover have a second surface traction, and wherein the second surface traction is lower than the first surface traction.

26. The membrane product package of claim 1, wherein the traction-creating feature of the product receiving portion comprises a rough top surface.

27. A method of producing a membrane product package, comprising:
positioning a membrane in an operative position between a product receiving portion of a base and a cover, wherein the membrane is positioned in engagement with at least a portion of a top surface of the product receiving portion of the base and at least a portion of a bottom surface of the cover, and wherein the membrane is a placental tissue product, a tissue graft, an in vitro cultured graft, a tendon graft, or a bioengineered membrane comprising living cells, and
wherein the product receiving portion of the base comprises a traction-creating feature, and wherein the traction-creating feature comprises one or more of the following: (i) a rough top surface, (ii) a plurality of perforations extending between the top and bottom surfaces of the product receiving portion, (iii) a surface comprising a plurality of channels, (iv) a surface comprising a plurality of grooves, (v) a surface comprising a plurality of indentations, or (vi) a surface comprising a plurality of porations.

28. The method of claim 27, wherein the step of positioning the membrane in the operative position comprises:
attaching the membrane to the top surface of the product receiving portion at least one attachment point; and
attaching the membrane to the cover at least one attachment point.

29. The method of claim 28, wherein the traction-creating feature of the product receiving portion of the base comprises a plurality of perforations, wherein the method further comprises positioning the base, the membrane, and the cover within a cryopreservation solution, wherein the plurality of perforations of the product receiving portion provide contact between the membrane and the cryopreservation solution sufficient to cryopreserve the membrane.

30. A kit for repairing a tissue defect, comprising:
a container; and
a membrane product package positioned within the container, the membrane product package comprising:
(a) a support assembly having:
(i) a base having a longitudinal axis and comprising a product receiving portion, the product receiving portion having a top surface and an opposed bottom surface that are spaced apart relative to a vertical axis that is perpendicular to the longitudinal axis of the base, wherein the product receiving portion comprises a traction-creating feature, wherein the traction creating feature is selected from the group consisting of (i) a rough top surface, (ii) a plurality of plurality of perforations extending between the top and bottom surfaces of the product receiving portion, (iii) a surface comprising a plurality of channels, (iv) a surface comprising a plurality of grooves, (v) a surface comprising a plurality of indentations, or (vi) a surface comprising a plurality of porations; and
(ii) a cover having a longitudinal axis, a top surface, and an opposed bottom surface, wherein the cover is configured for releasable coupling to the base in a product-covering position, and wherein, in the product-covering position, the cover overlies the product receiving portion of the base; and
(b) a membrane positioned in an operative position between the product receiving portion of the base and the cover, wherein the membrane is positioned in engagement with at least a portion of the top surface of the product receiving portion of the base and at least a portion of the bottom surface of the cover, and wherein the membrane is a placental tissue product, a tissue graft, an in vitro cultured graft, a tendon graft, or a bioengineered membrane comprising living cells,
wherein the base and the cover cooperate to support the membrane in the operative position.

31. The kit of claim 30, further comprising a cryopreservation solution.

* * * * *